(12) United States Patent
Egli

(10) Patent No.: US 10,351,876 B2
(45) Date of Patent: Jul. 16, 2019

(54) METHODS FOR MAKING AND USING MODIFIED OOCYTES

(71) Applicant: New York Stem Cell Foundation, Inc., New York, NY (US)

(72) Inventor: Dietrich M. Egli, New York, NY (US)

(73) Assignee: New York Stem Cell Foundation, Inc., New York, NY (US)

( * ) Notice: Subject to any disclaimer, the term of this patent is extended or adjusted under 35 U.S.C. 154(b) by 97 days.

(21) Appl. No.: 15/253,781

(22) Filed: Aug. 31, 2016

(65) Prior Publication Data

US 2017/0114366 A1    Apr. 27, 2017

Related U.S. Application Data

(63) Continuation of application No. 14/098,424, filed on Dec. 5, 2013, now Pat. No. 9,434,960.

(60) Provisional application No. 61/793,234, filed on Mar. 15, 2013, provisional application No. 61/734,299, filed on Dec. 6, 2012.

(51) Int. Cl.
| | |
|---|---|
| *C12N 15/00* | (2006.01) |
| *C12N 15/873* | (2010.01) |
| *C12N 5/075* | (2010.01) |
| *C12N 5/16* | (2006.01) |
| *C12N 15/877* | (2010.01) |
| *A61K 35/54* | (2015.01) |
| *C12N 7/00* | (2006.01) |

(52) U.S. Cl.
CPC ............ *C12N 15/873* (2013.01); *A61K 35/54* (2013.01); *C12N 5/0609* (2013.01); *C12N 5/16* (2013.01); *C12N 7/00* (2013.01); *C12N 15/8775* (2013.01); *C12N 15/8776* (2013.01); *C12N 2517/04* (2013.01); *C12N 2517/10* (2013.01); *C12N 2760/18832* (2013.01)

(58) Field of Classification Search
CPC . C12N 5/0609; C12N 15/8776; C12N 5/0604
USPC ................................................. 800/24, 14
See application file for complete search history.

(56) References Cited

FOREIGN PATENT DOCUMENTS

WO    WO 2010124123 A1 * 10/2010

OTHER PUBLICATIONS

Tarkowski (J. Embryol, exp. Morph, 55:319-330, 1980.*
Meirelles, Genetics, 2001, 158:351-356.*
Brown, Lancet, 2006,368:87-89.*
Roberts, 1999, American Journal of Medical Genetics, 57:265-266.*
Tachibana(A), Nature, 2009, 461:367-372; provided as pp. 1-14.*
Di Berardino, Methods in Molecular Biology, Nuclear Transfer Protocols, Human Press, Totowa NJ, 2006, Ed., Verma and Trounson, pp. 1-31.*
Aman: "Effects of cooling and rewarming on the meiotic spindle and chromosomes of in vitro-matured bovine oocytes"; 1994, Biology of Reproduction, 50:103-110.
Bianchi: "Meiotic spindle imaging in human oocytes frozen with a slow freezing procedure involving high sucrose concentration"; 2005, Human Reproduction, 20:1078-1083.
Craven et al.: 'Pronuclear transfer in human embryos to prevent transmission of mitochondria' DNA disease'; Nature, vol. 465, No. 7294, p. 82-85, May 6, 2010.
Extended European Search Report dated Jun. 29, 2016, regarding EP 13859745.5.
Hyun et al.: "Optimal ICS' timing after the first polar body extrusion in in vitro matured human oocytes"; Hum Reprod., vol. 22, No. 7, p. 1991-1995,. May 18, 2007.
International Search Report dated Feb. 20, 2014 regarding PCT/US2013/073423.
Kuczynski: "Rescue ICSI of unfertilized oocytes after IVF"; Human Reproduction, 2002, 7:2423-2427.
Paull, D. et al.: "Nuclear genome transfer in human oocytes eliminates mitochondria! DNA variants"; Nature, vol. 493, No. 7434, p. 632-637.
Tachibana et al.: "Towards germline gene therapy of inherited mitochondria' diseases"; Nature,. vol. 493, No. 7434, pp. 627-631. Oct. 2012.
Takeuchi, T., et al.: "Preliminary findings in germinal vesicle transplantation of immature human oocytes"; Human Reproduction, vol. 16, No. 4, pp. 730-736. Published Online on Apr. 1, 2001.
Tanaka, A., et al.: "Metaphase 11 karyoplast transfer from human in-vitro matured oocytes to enuclueated mature oocytes"; Reproductive Biomedicine Online, Reproductive Healthcare Ltd, GB, vol. 19, No. 4, pp. 514-520.
Yabuuchi et al.: "Prevention of mitochondria! disease inheritance by assisted reproductive technologies: Prospects and challenges"; Biochim Biophys Acta., vol. 1820, No. 5, p. 637-1642.
Calarco, Patricia G. "The Role of Microfilaments in Early Meiotic Maturation of Mouse Oocytes"; Microsc, Microanal., 2005, vol. 11, pp. 146-153.
European Examination Report dated Mar. 5, 2018, regarding EP 13 859 745.5.

* cited by examiner

*Primary Examiner* — Valarie E Bertoglio
(74) *Attorney, Agent, or Firm* — DLA Piper LLP (US)

(57) ABSTRACT

The present invention provides modified oocytes having a nuclear genome derived from a first oocyte and cytoplasm derived from a second oocyte from a different subject, and methods for making and using such modified oocytes. The methods and compositions of the present invention can be useful in a variety of settings including, but not limited to, in in vitro fertilization ("IVF") procedures.

29 Claims, 15 Drawing Sheets

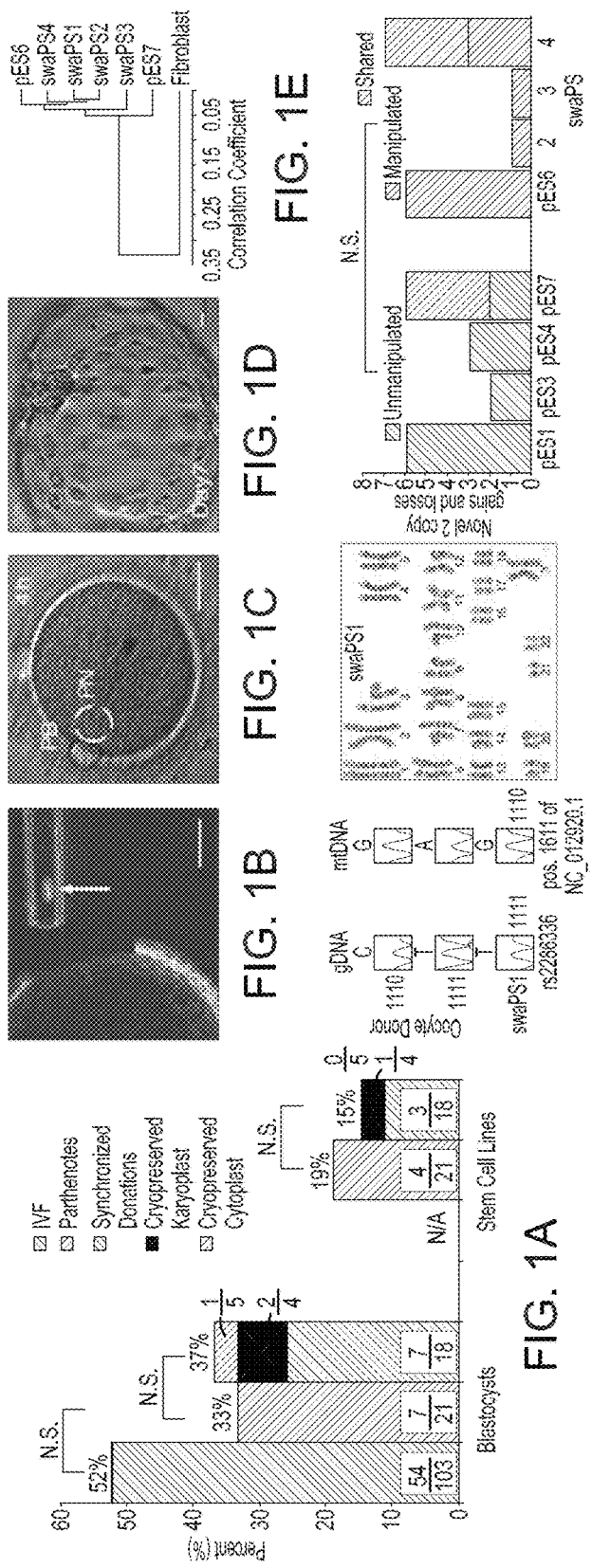

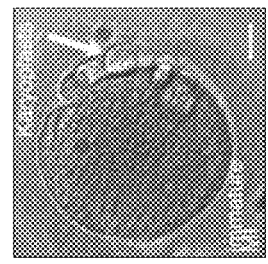
FIG. 2A
FIG. 2B
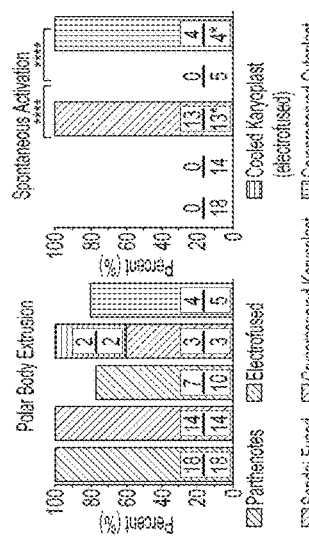
FIG. 2C
FIG. 2D
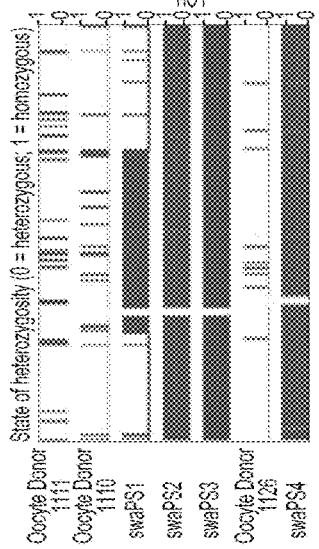
FIG. 2E
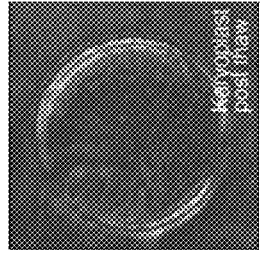
FIG. 2F
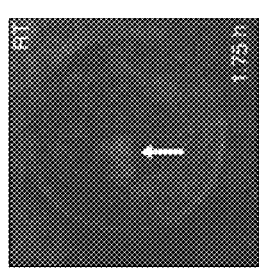
FIG. 2G
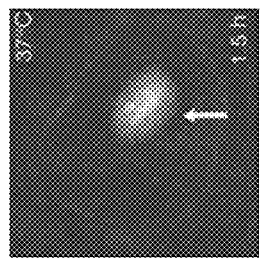
FIG. 2H
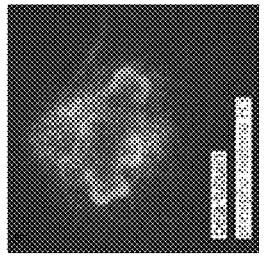
FIG. 2I
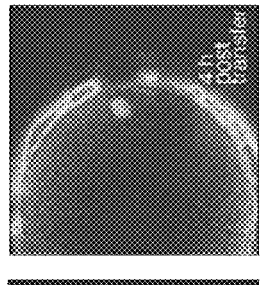
FIG. 2J
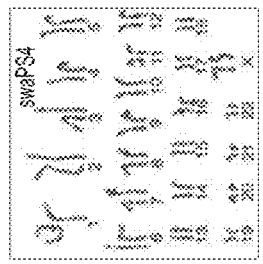
FIG. 2K

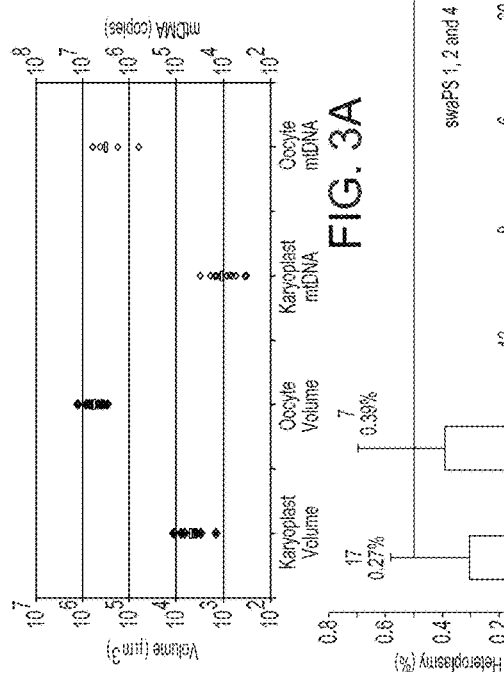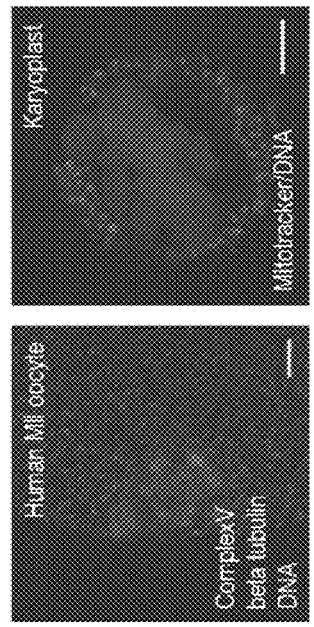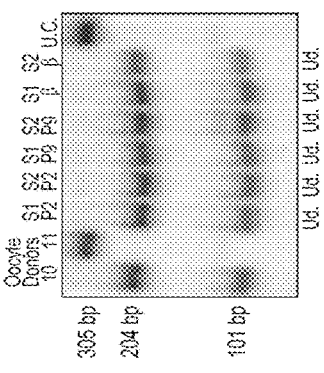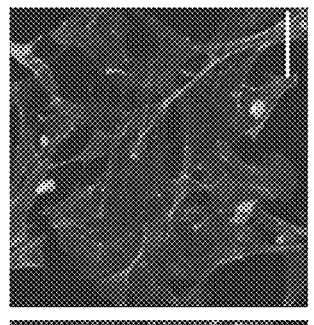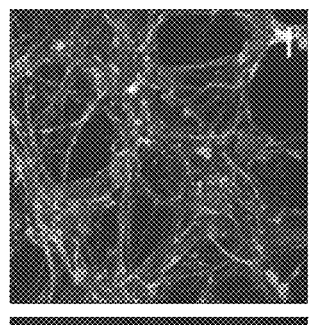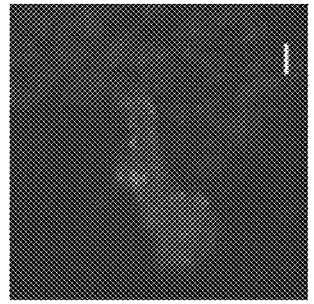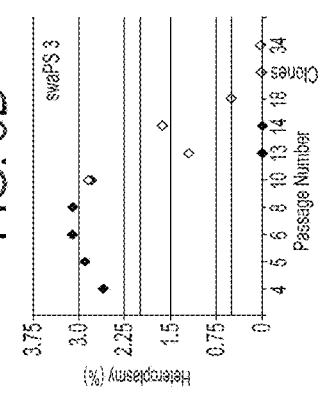
FIG. 3A FIG. 3B FIG. 3C FIG. 3D FIG. 3E FIG. 3F FIG. 3G FIG. 3H FIG. 3I

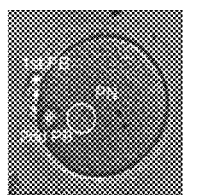  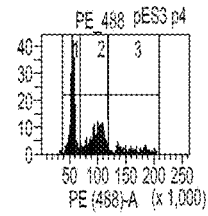 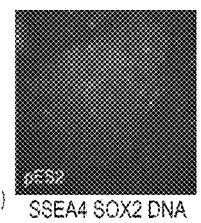 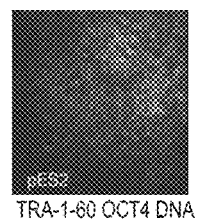
FIG. 7A   FIG. 7B   FIG. 7C   FIG. 7D   FIG. 7E
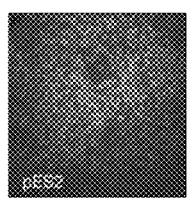 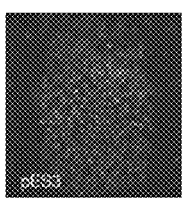 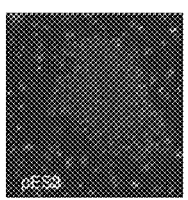 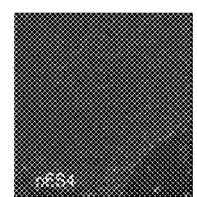 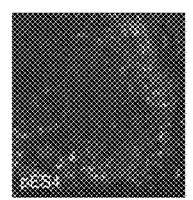
FIG. 7F   FIG. 7G   FIG. 7H   FIG. 7I   FIG. 7J
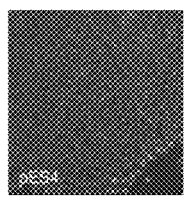 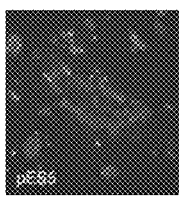 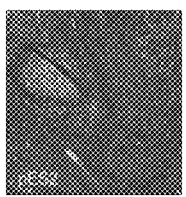 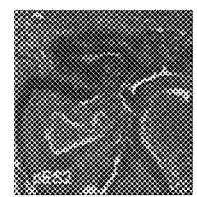 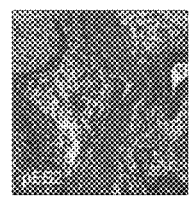
FIG. 7K   FIG. 7L   FIG. 7M   FIG. 7N   FIG. 7O
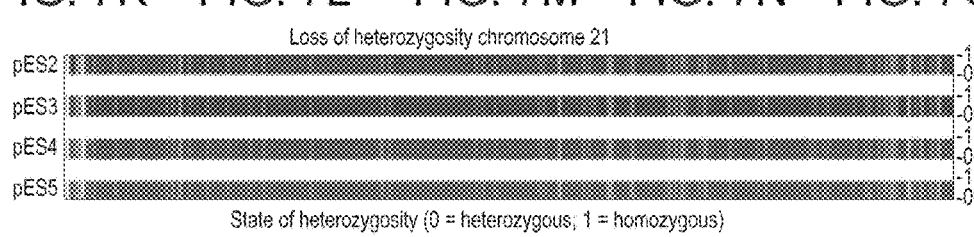
FIG. 7P
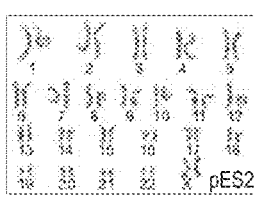 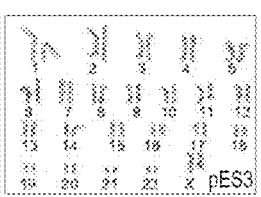 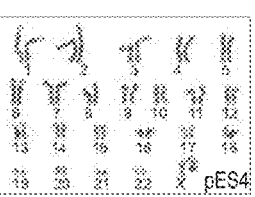 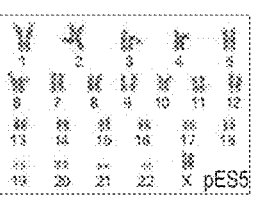
FIG. 7Q   FIG. 7R   FIG. 7S   FIG. 7T

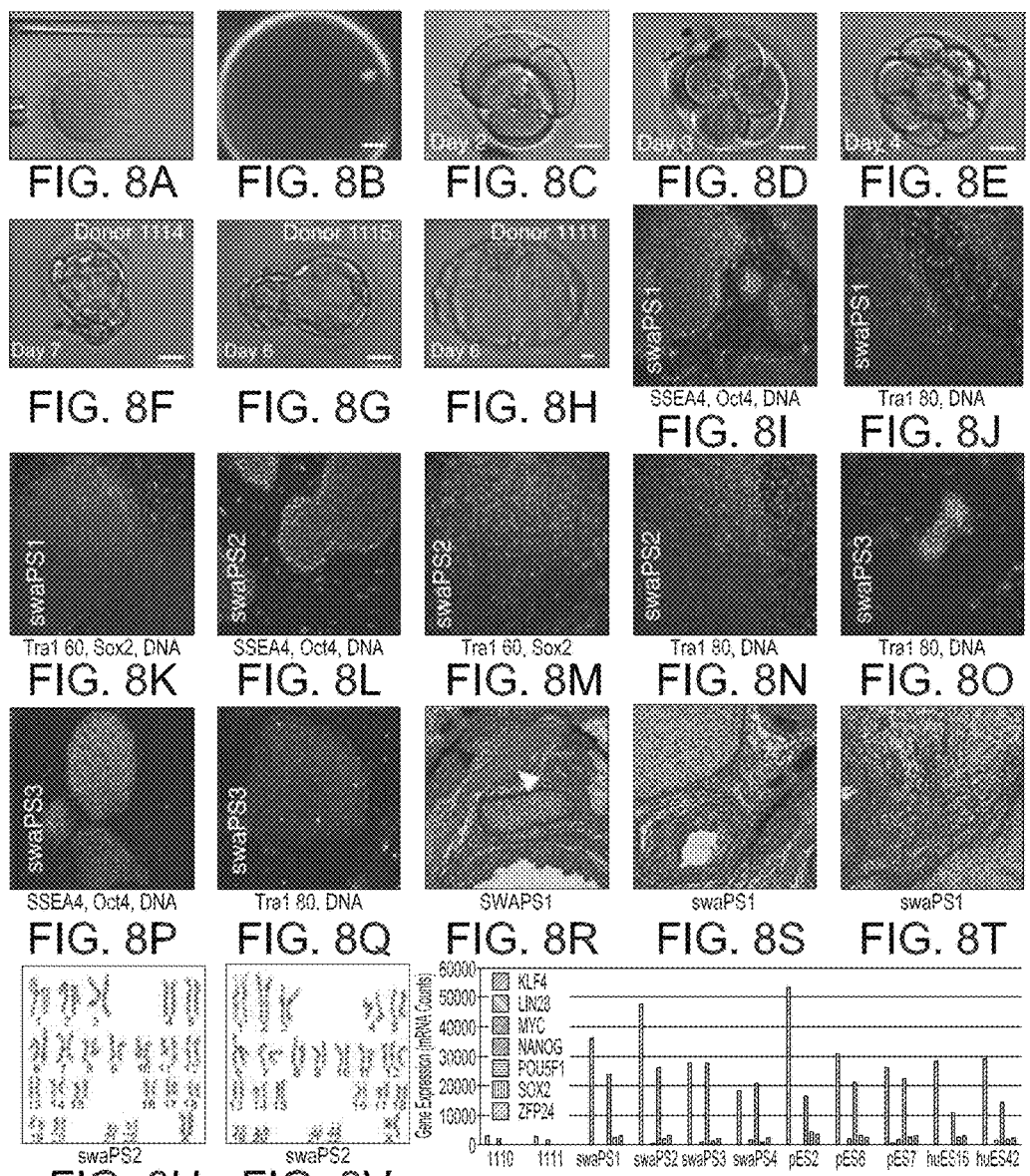

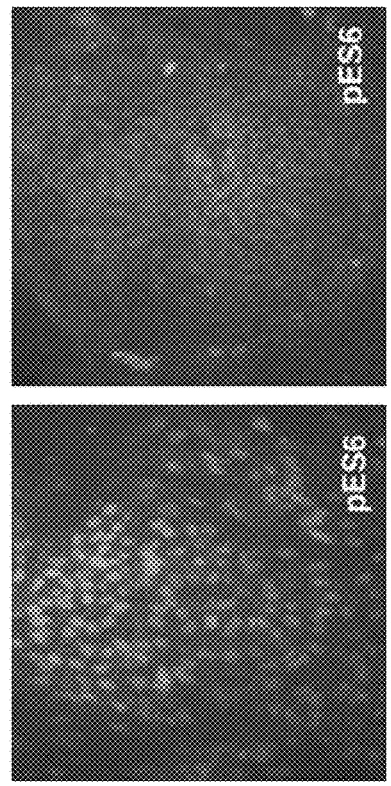
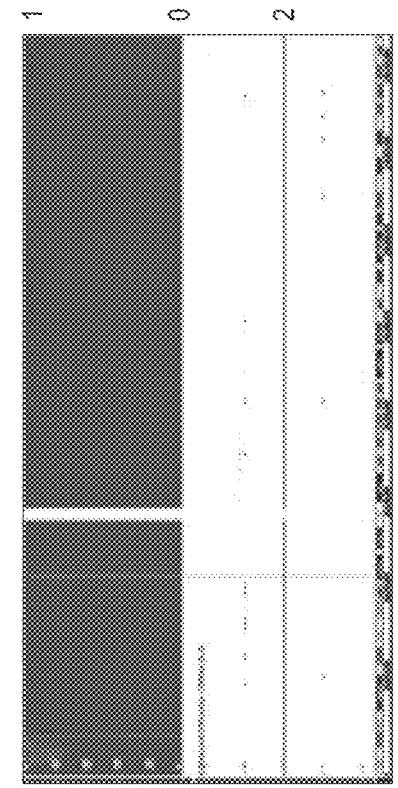
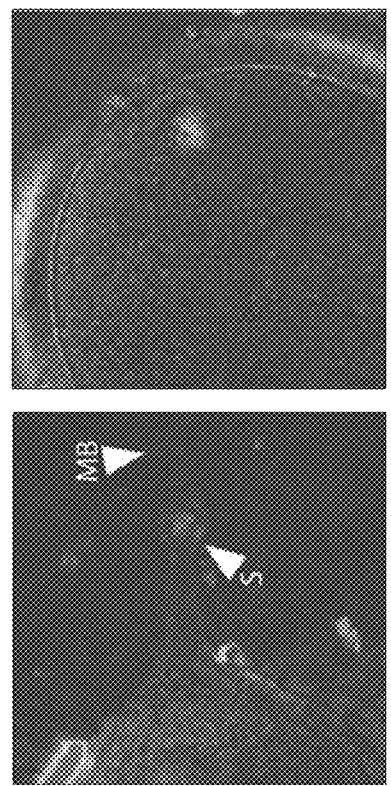
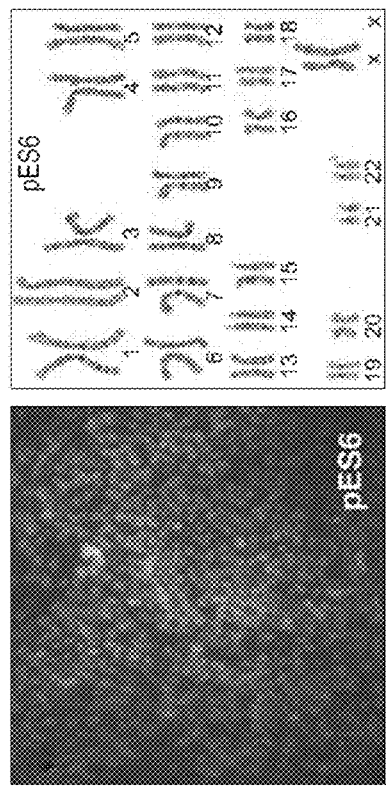

SOX2, SSEA4, DNA

NANOG, DNA

OCT4, TRA-1-60, DNA

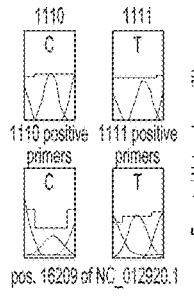
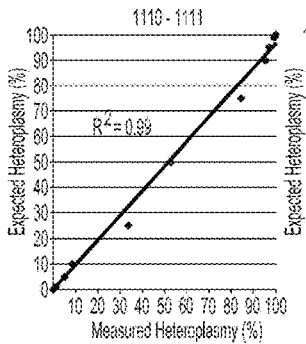
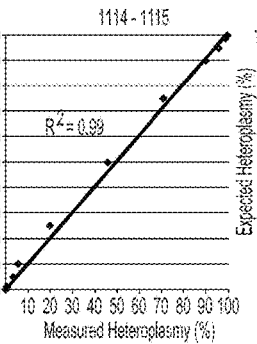
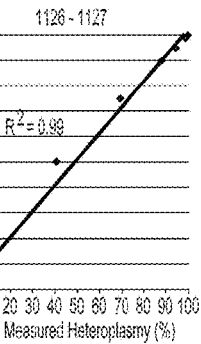
FIG. 13A   FIG. 13B   FIG. 13C   FIG. 13D
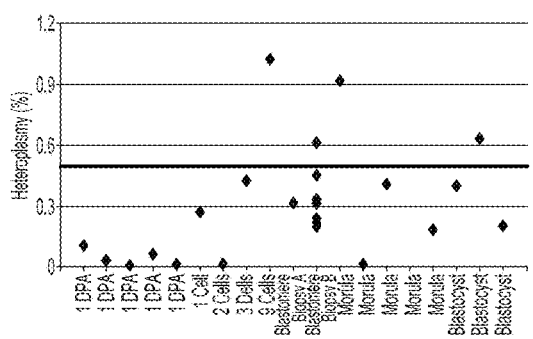
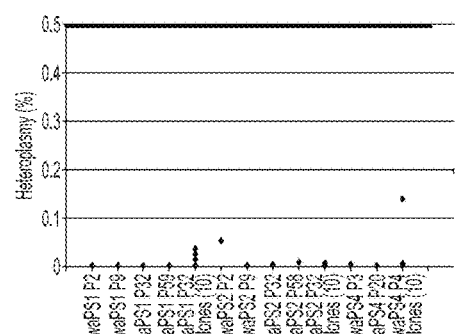
FIG. 13E   FIG. 13F
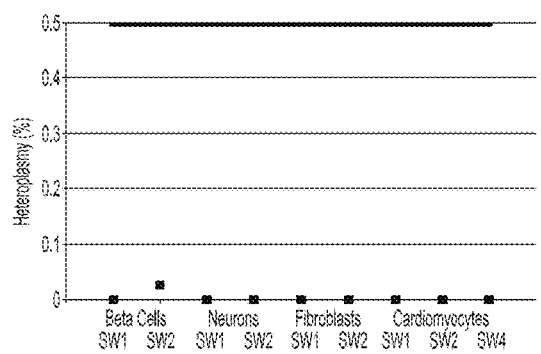
FIG. 13G

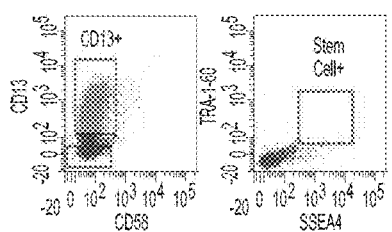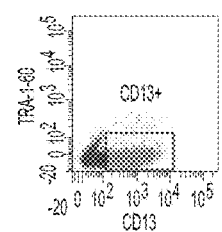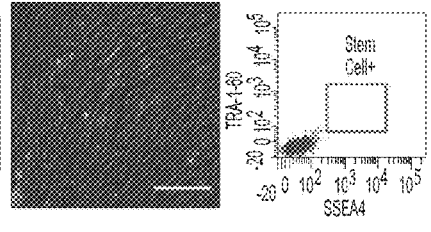
FIG. 14A    FIG. 14B    FIG. 14C
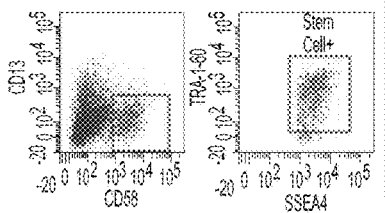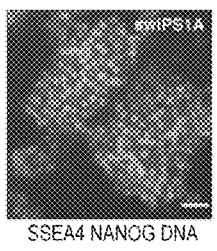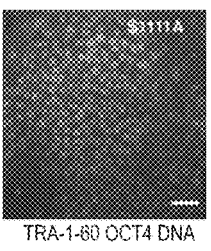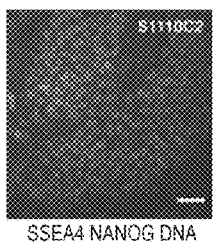
FIG. 14D    FIG. 14E    FIG. 14F    FIG. 14G
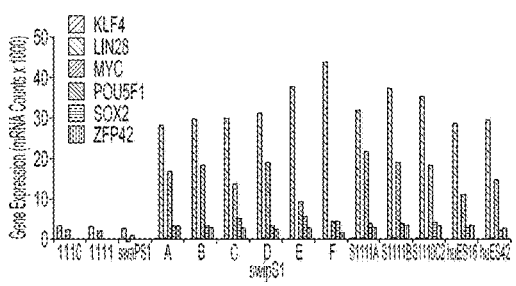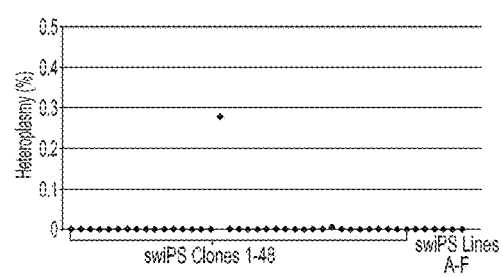
FIG. 14H    FIG. 14I
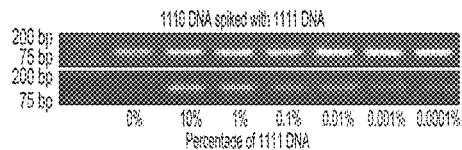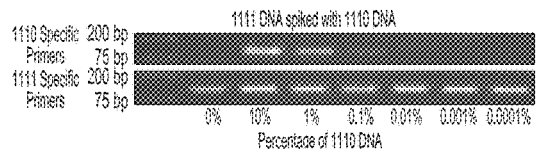
FIG. 14J
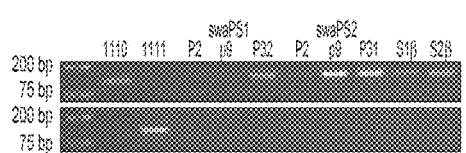
FIG. 14K

METHODS FOR MAKING AND USING MODIFIED OOCYTES

CROSS-REFERENCE TO RELATED APPLICATIONS

This application is a continuation application of U.S. application Ser. No. 14/098,424 filed Dec. 5, 2013, now issued as U.S. Pat. No. 9,434,960; which claims the benefit under 35 USC § 119(e) to U.S. Application Ser. No. 61/793,234 filed Mar. 15, 2013 and to U.S. Application Ser. No. 61/734,299 filed Dec. 6, 2012. The disclosure of each of the prior applications is considered part of and is incorporated by reference in the disclosure of this application.

BACKGROUND OF THE INVENTION

Copyright

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

INCORPORATION BY REFERENCE

For countries and territories that permit incorporation by reference, the text of all documents cited herein is hereby incorporated by reference in its entirety.

FIELD OF THE INVENTION

The present invention involves modified oocytes having a nuclear genome derived from a first oocyte and cytoplasm derived from a second oocyte, and methods and kits for making and using such modified oocytes. The modified oocytes and methods of the present invention can be useful in a variety of settings including, but not limited to, in in vitro fertilization ("IVF") fertility procedures.

BACKGROUND INFORMATION

There is a need in the art for methods of making and using modified oocytes. For example, there is a need in the art for methods of making and using modified oocytes as a means for avoiding or eliminating the inheritance of deleterious mutations of the mitochondrial genome. Mitochondrial DNA mutations transmitted maternally within the oocyte cytoplasm often cause life-threatening disorders. A critical determinant of the phenotypic severity in most maternally inherited mitochondrial diseases is heteroplasmy, i.e., the proportion of mutant, relative to total, mitochondrial DNA (mtDNA) within a cell. Due to the cytoplasmic segregation of mitochondria during cell division, the level of heteroplasmy is subject to broad fluctuations, in particular during the developmental expansion of mtDNA from the premeiotic germ cell to the mature human oocyte. As a result, an unaffected carrier of a mtDNA mutation may have an affected child. Whilst prenatal genetic diagnosis can select embryos with a reduced mutation load, variation between blastomeres in single embryos limits the effectiveness of such screening, and significant levels of mutant mtDNA can remain resulting in a carrier. Because of such issues, the Nuffield Council on Bioethics has endorsed research to prevent transmission of mtDNA mutations, including the transfer of the nuclear genome of one oocyte into an enucleated oocyte containing normal mitochondria.

Another area in which there is a need in the art for methods of making and using modified oocytes is in the area of fertility treatment. In vitro fertilization ("IVF") treatments fail at increased rates as maternal age increases, at least in part because the developmental potential of oocytes decreases with advancing maternal age. In women above the age of forty-two with the ability to hyperstimulate, the IVF success rate falls to less than 5% of live births and miscarriage rates approach 50%, with a high aneuploidy rate. This is both a significant clinical problem as well as source of personal suffering to prospective parents. The causes of this drop in fertility include a decreased quality of the oocytes. Oocytes are less likely to be fertilized, are more likely to contain aneuploidies, less likely to implant (Piette et al. 1990), and more likely to result in spontaneous abortion or congenital abnormalities. They are also less in number. Many of the developmental defects arise as a consequence of abnormal chromosome segregation in mitoses of preimplantation stage embryos, and at the first and second meiotic division. The number of oocytes obtained from women of advanced maternal age is often also reduced (Piette et al. 1990), thereby further reducing the chance of a successful pregnancy.

A decline in developmental potential also occurs when oocytes remain unfertilized for prolonged periods either in vitro or in vivo: the timing for optimal fertilization and development in mice is less than 12 hours post ovulation (see, for example, Woods et al. 1990; Wakayama et al. 2004; Ono et al. 2011), and in humans is within 4 to 12 hours after ovulation or oocyte retrieval (see, for example, Morton et al. 1997; Chen and Kattera 2003). In vitro postovulatory aging of oocytes occurs during prolonged in vitro culture of oocytes before fertilization, and is a clinically important issue. Failure to fertilize oocytes occurs in approximately 5% to 10% of conventional IVF cycles, and on average 15-30% of oocytes remain unfertilized even with fully functional sperm (see, for example, Barlow et al. 1990; Nagy et al. 1993). Generally oocytes that have not been successfully fertilized in an IVF cycle cannot be used in subsequent IVF cycles. The rate of pregnancy and implantation rates decreases to 5-20% and 1.7%, respectively, at 62 hours post human chorionic gonadotropin (hCG) treatment when oocytes are aged in vitro, while the corresponding rates are 48.0% and 20.2%, respectively, at 46 hours post-hCG treatment (Yuzpe et al. 2000; Chen and Kattera 2003).

Approximately 10-30% of oocytes are immature at retrieval from the ovary, at either the metaphase I or the germinal vesicle stage. While about half of them mature to the MII stage within hours after retrieval, and are useful for IVF treatments, many oocytes remain arrested at the germinal vesicle stage. And those that can be matured to the metaphase II stage often have a reduced developmental competence compared to oocytes that are already mature when they are retrieved from the ovary. This is why immature oocytes are generally not used for IVF treatments and instead are discarded. The loss of these oocytes reduces the chance of successful IVF treatments, especially for women of advanced age, who may start out with a lower total number of retrieved oocytes. Failure to mature to the MII stage can also be a medical condition, where all oocytes fail to mature, resulting in infertility (Chen et al. 2010).

Currently, after exhausting other available options, women who are unsuccessful with fertility treatments, such as in vitro fertilization treatments, using their own eggs sometimes resort to using oocyte donors to achieve a pregnancy—even though the children born from such pregnancies are not genetically related to the mother. There is a need in the art to develop a better understanding of the molecular events that lead to reduced developmental potential of oocytes with maternal age, and also with increased culture time in vitro, and a need for new methods that could improve the developmental potential of such oocytes, allow rescue of oocytes from failed IVF treatments, and give women who have been unable to achieve pregnancy using traditional in vitro fertilization methods another chance at becoming pregnant with a child that is genetically related to her.

SUMMARY OF THE INVENTION

In some embodiments the present invention provides modified oocytes having a nuclear genome derived from an oocyte of one female (a first oocyte), and cytoplasm derived from an oocyte obtained from a different female (a second oocyte), and methods for making and using such modified oocytes. The methods and compositions of the present invention can be useful in a variety of different areas. One application of such modified oocytes and methods is in the fertility treatment field—whereby, for example, a nuclear genome may be transferred from a first developmentally incompetent oocyte (such as from an infertile female) to a second enucleated developmentally competent oocyte (such as from a fertile female). Another application of such modified oocytes and methods involves transfer a nuclear genome from a first oocyte that has some kind of defect or abnormality to a second oocyte that does not have that defect or abnormality. Such defects or abnormalities could include, for example, cytoplasmic defects, defects in the cell membrane, defects in the mitochondrial genome (such as deleterious and/or disease-causing mitochondrial mutations), and the like.

The present invention also provides several techniques for nuclear transfer that represent improvements compared to prior nuclear transfer methods and that are useful in making the modified oocytes of the invention. For example, in some embodiments, the present invention provides improved nuclear transfer methods that involve performing nuclear transfer at specific phases of the meiotic cycle and/or when meiotic spindles are present in a certain state. Such methods differ from those taught previously and result in improved outcomes following nuclear transfer. Further details of these new and improved nuclear transfer protocols, and methods of making and using modified oocytes using such protocols, are provided in the present Summary of the Invention as well as throughout other sections of this patent application—including the Detailed Description, Drawings, Examples and Claims. One of skill in the art will appreciate that various different embodiments of the invention, or aspects of such embodiments, may varied or combined in various ways without departing from the spirit of the invention. Such variations and combinations fall within the scope of the present invention.

In one embodiment the present invention provides a method for producing a modified oocyte having improved developmental competence, the method comprising: obtaining a nuclear genome from a developmentally incompetent first oocyte, removing the nuclear genome from a developmentally competent second oocyte to form an enucleated second oocyte (cytoplast), and introducing the nuclear genome from the first oocyte into the cytoplast to form a modified oocyte.

In another embodiment the present invention provides an in vitro fertilization method for use with incompetent oocytes, the method comprising: obtaining a nuclear genome from a developmentally incompetent first oocyte, removing the nuclear genome from a developmentally competent second oocyte to form an enucleated second oocyte (cytoplast), introducing the nuclear genome from the first oocyte into the cytoplast to form a modified oocyte, and fertilizing the modified oocyte in vitro to form a zygote.

In another embodiment, the present invention provides an in vitro method for producing an embryo from a developmentally incompetent oocyte, the method comprising: obtaining a nuclear genome from a developmentally incompetent first oocyte, removing the nuclear genome from a developmentally competent second oocyte to form an enucleated second oocyte (cytoplast), introducing the nuclear genome from the first oocyte into the cytoplast to form a modified oocyte, fertilizing the modified oocyte in vitro to form a zygote, and culturing the zygote in vitro to form an embryo.

In one embodiment the present invention provides a method for producing a modified oocyte, comprising: (a) obtaining a nuclear genome from a first oocyte, wherein the nuclear genome has not yet reached the mature metaphase II stage or is an immature metaphase II nuclear genome or is a metaphase II nuclear genome that has been treated to induce partial spindle depolymerization, (b) removing the nuclear genome from a second oocyte to form an enucleated second oocyte, and (c) introducing the nuclear genome from the first oocyte into the enucleated second oocyte to form a modified oocyte. In some such embodiments the nuclear genome from the first oocyte is an immature metaphase II nuclear genome obtained within 2 hours after extrusion of a first polar body or before complete assembly of a metaphase II spindle. In some such embodiments the treatment to induce partial spindle depolymerization may comprise cryopreserving the first oocyte or the nuclear genome, maintaining the oocyte or the nuclear genome at room temperature for a period of time (for example up to 4 hours), or contacting the first oocyte or the nuclear genome with a microtubule depolymerizing agent.

In some embodiments the present invention provides methods for use with oocytes from any mammalian species. In some embodiments, the claimed methods can utilize murine oocytes, such as mouse oocytes. In other embodiments the claimed methods can utilize primate oocytes, such as human oocytes or oocytes from a non-human primate species. The oocyte from which the nuclear genome is obtained, and the oocyte into which the nuclear genome is transferred, should be from animals of the same species.

In some embodiments the nuclear genome used in the methods of the invention comprises the nuclear DNA of an oocyte, for example in the form of chromosomes. In some embodiments the nuclear genome may be within a "karyoplast" that comprises the nuclear DNA and a small amount of cytoplasm surrounded by a membrane, such as nuclear membrane and/or cell membrane. The nuclear genome may be without a surrounding membrane, and without cytoplasm.

In some embodiments the first oocyte, the second oocyte, or both the first and second oocytes used in the methods described herein, may have been previously cryopreserved. Similarly, in some embodiments the donor nuclear genome used in the claimed methods may have been previously cryopreserved (for example as within a karyoplast, within the zona pellucida of an oocyte, or within a small artificially formed karyoplast container, such as a plastic vessel) and/or the enucleated oocyte from which the cytoplasm is obtained may have been previously cryopreserved (for example in the form of a cytoplast). In alternative embodiments fresh (i.e., not previously cryopreserved) oocytes, nuclear genomes, karyoplasts, enucleated oocytes and/or cytoplasts may be used in the methods of the invention.

In some embodiments the oocytes used in the claimed methods are obtained from a woman or mammal at some desirable time point in their developmental cycle, such as at some desirable time point either before or after ovulation, or specific stage of oocyte maturation. In some embodiments the claimed methods may be used in conjunction with medical and/or veterinary treatments used to synchronize and/or stimulate ovulation. When human oocytes are used they may be obtained from a subject following treatment of the subject with a hormone or other drug used to stimulate ovulation, such as hCG. In some embodiments the oocytes are obtained from a human subject 30 to 40 hours after administration of an ovulation stimulus, such as hCG or leuprolide acetate, to the subject.

In some embodiments the first oocyte from which the nuclear genome is obtained, is derived from an older subject and the second oocyte from which the cytoplasm is used is obtained from a younger subject. For example, where the nuclear genome is derived from a human female, the subject may be older than 30, 35, 40, 45, 50 or more years old. Conversely, when the cytoplasm is derived from a human female, the subject may younger, such as less than 35, 30, 25, or 20 years old, or even younger. In some embodiments the oocyte from which the nuclear genome is obtained, is derived from a subject that is infertile or has reduced or suboptimal fertility, such as infertility or reduced fertility associated with a defect or deficiency in one or more cytoplasmic factors. In some embodiments the oocyte from which the nuclear genome is obtained, is derived from a subject that has had problems achieving fertilization, embryo development, implantation or pregnancy—either naturally and/or using one or more assisted reproduction methods (such as IVF). In some embodiments the oocyte from which the nuclear genome is obtained, has been in vitro for an excessive period of time without being fertilized. In some embodiments the present invention provides a method of treating infertility in a subject, the method comprising using a modified oocyte as described herein, or a modified oocyte prepared using the methods described herein, in an assisted reproduction procedure, including, but not limited to, an IVF procedure.

In some embodiments the first oocyte from which the nuclear genome is obtained comprises a mutation in its mitochondrial DNA (such as a mutation that causes a disease) and the second oocyte does not comprise the mutation in its mitochondrial DNA. In some embodiments the first oocyte from which the nuclear genome is obtained is from a subject that has a disease caused by a mitochondrial DNA mutation and the second oocyte is obtained from a subject that does not have that disease. In some embodiments the present invention provides a method of treating or preventing a disease caused by a mitochondrial DNA mutations in a subject, the method comprising using a modified oocyte as described herein, or a modified oocyte prepared using the methods described herein, in an assisted reproduction procedure, including, but not limited to, an IVF procedure.

In embodiments that comprise introducing a nuclear genome from a first oocyte into an enucleated second oocyte (cytoplast), the step of "introducing" the nuclear genome can be facilitated by using an electrical pulse or a fusogenic agent to fuse the donor nuclear genome (typically comprised in a karyoplast) with the recipient oocyte. In embodiments where a fusogenic agent is used exemplary fusogenic agents include, but are not limited to, a Sendai virus (such as an inactivated Sendai virus) or polyethylene glycol. The nuclear genome may also be injected directly into the oocyte, for example using a glass pipette.

In some embodiments a nuclear genome for use in the methods of the invention (i.e., to be transferred into a cytoplast) is obtained from a first oocyte that is at some particular phase of its development and/or at some particular phase of the meiotic cycle. For example, in one embodiment the nuclear genome is obtained from a germinal vesicle nucleus. In another embodiment the nuclear genome is obtained from a metaphase I oocyte. In another embodiment the nuclear genome is obtained from an immature metaphase II oocyte, or before assembly of a mature metaphase II spindle. In another embodiment the nuclear genome is obtained from a mature metaphase II oocyte. Indeed, it is a finding of the present invention that transfer of a nuclear genome from a first oocyte into an enucleated second oocyte can be achieved more efficiently, and can lead to improved developmental competence of a resultant modified oocyte, if the nuclear genome is used at particular stage of the meiotic cycle or with its genome in a particular state. For example, in some embodiments it may be preferable to obtain a nuclear genome from an oocyte before formation of a mature metaphase II meiotic spindle, for example, by obtaining the nuclear genome from an immature metaphase II oocyte within 2 hours after extrusion of the first polar body or before complete assembly of the metaphase II spindle. In other embodiments it may be preferable to obtain a nuclear genome from a mature metaphase II oocyte but to first treat the oocyte (or the nuclear genome obtained from the oocyte) to induce partial spindle de-polymerization, for example using cryopreservation and/or by maintaining the mature metaphase II oocyte/genome at room temperature for some period of time (such as up to 4 hours, or up to 2 hours, or from 1-2 hours), or by contacting the mature metaphase II oocyte/genome with a microtubule depolymerizing agent (such as nocodazole or vinblastine).

In some embodiments an enucleated second oocyte for use in the methods of the invention is obtained, or enucleated, when it is at some particular phase of its development and/or at some particular phase of its meiotic cycle. For example, in one embodiment the enucleated second oocyte is obtained from a metaphase I (MI) oocyte. In another embodiment the enucleated second oocyte is obtained from an immature MI oocyte, before or during spindle assembly. In another embodiment, the enucleated second oocyte is obtained after arresting the oocyte at metaphase I using nocodazole or another spindle depolymerizing agent. In another embodiment the enucleated second oocyte is obtained from an immature metaphase II oocyte. In another embodiment the enucleated oocyte is obtained from a mature metaphase II oocyte. In some embodiments the enucleated second oocyte is obtained before formation of a mature meiotic spindle during metaphase II, for example, by enucleating a recipient oocyte from an immature metaphase II oocyte within 2 hours after extrusion of the first polar body or before complete assembly of the metaphase II spindle. In another embodiment the enucleated recipient oocyte is obtained from a mature metaphase II oocyte that has been treated to induce spindle de-polymerization, for example using cryopreservation and/or by maintaining the mature metaphase II oocyte at room temperature for some period of time, such as up to 4 hours, or has been treated with nocodazole or another spindle depolymerizing agent.

In one embodiment the methods of the invention comprise transfer of a nuclear genome from a mature metaphase II oocyte to an enucleated mature metaphase II oocyte. In another embodiment the methods of the invention comprise transfer of a nuclear genome from mature or immature metaphase II oocyte to an enucleated immature metaphase II oocyte (wherein the oocyte is considered immature for 1-2 hours after extrusion of the first polar body, or for as long as a metaphase II spindle has not yet been fully assembled). The enucleation of the oocyte may be done at any stage between anaphase of the first meiosis, and the assembly of a fully mature metaphase II spindle. A mature spindle is defined as a spindle where all chromosomes are aligned on the metaphase plate, with bipolar attachment of all chromosomes to microtubules. In another embodiment the methods of the invention comprise transfer of a nuclear genome from a metaphase I oocyte to an enucleated metaphase I oocyte, followed by in vitro maturation of the resulting modified oocyte to a metaphase II stage oocyte. In another embodiment the methods of the invention comprise transfer of a germinal vesicle (GV) nucleus (containing a nuclear genome) from a first oocyte into a second enucleated metaphase I oocyte. The metaphase I oocyte may be enucleated at any time after germinal vesicle breakdown, until the assembly of a mature metaphase I spindle.

In some embodiments the methods of the present invention involve taking a modified oocyte formed by the transfer of a nuclear genome from a first oocyte into an enucleated second oocyte and fertilizing the modified oocyte. In some embodiments the modified oocyte may be fertilized in vivo (for example after placement of the modified oocyte into a reproductive tract). In other embodiments the modified oocyte may be fertilized in vitro, such as using an IVF method. Where the sperm to be used in the IVF method are of sufficient quality and competence a standard IVF protocol may be used. Where the sperm to be used in the IVF methods are of suboptimal quality or are incompetent to some degree, the IVF method used may involve intracytoplasmic sperm injection (ICSI). ICSI may also be used with normal sperm to increase the chance of fertilization. In some embodiments, following fertilization of a modified oocyte a zygote is formed. In some embodiments the zygote is cultured to form an embryo, such as a 2-cell embryo, a 4-cell embryo, an 8-cell embryo, a morula, or a blastocyst. In some embodiments the embryo is subsequently inserted into a suitable region of the reproductive tract of a female subject (such as the fallopian tubes or uterus) with the hope that the embryo might implant, establish a pregnancy, and ultimately develop into a viable fetus and lead to the birth of live offspring. Typically the embryo will be inserted into the subject's reproductive tract when it is at the cleavage stage, or at the blastocyst stage, or between day 3 and day 6 after fertilization. The subject into whose reproductive tract the embryo is inserted may be the same subject from whom the nuclear genome of the oocyte was obtained or may be a different subject.

Other aspects of the present invention are either described elsewhere in the present application (such as the Examples), or are well known in the art. For example, methods for obtaining oocytes from a subject, the tools and equipment for manipulating oocytes, cryopreservation methods, IVF methods, in vitro embryo culture methods, and methods for placement of embryos in a patient's reproductive tract are well known in the art and any such suitable methods known in the art can be used in conjunction with the methods and compositions of the present invention.

BRIEF DESCRIPTION OF THE DRAWINGS

FIGS. 1A-1H. Efficient development and genomic integrity after nuclear genome exchange. FIG. 1A, Developmental potential of IVF embryos, parthenogenic and genome exchanged oocytes. Number in each bar displays the total number of oocytes developing to the indicated stage, of total oocytes. FIG. 1B, Removal of the karyoplast (indicated by arrow). FIG. 1C, Polar body (PB) extrusion and pronuclear (PN) formation.

FIG. 1D, Blastocyst stage. Scale bar: 25 μm. FIG. 1E, Cluster diagram of global gene expression profiles of swapped pluripotent stem cell lines (swaPS). FIG. 1F, Sanger sequences of gDNA and mtDNA. FIG. 1G, Karyotype of swaPS1 at passage 3. FIG. 1H, Copy number variation (CNV) analysis. pES=parthenogenetic ES cells. N.S.=no significant difference. See Example 1.

FIGS. 2A-2K. Spontaneous activation can be prevented through spindle cooling. FIG. 2A, Affymetrix SNP microarray (Chromosome 7). FIG. 2B, Array analysis at the cleavage stage, revealing trisomy on chromosome 4. FIG. 2C, Frequency of polar body extrusion. FIG. 2D, Frequency of manipulation-induced activation. *total oocytes confirmed. FIG. 2E, Karyoplasts after cryopreservation. FIG. 2F, FIG. 2G, FIG. 2H, Spindle birefringence at indicated temperatures and time points post thaw. Arrow indicates site of spindle. FIG. 2I, Confocal analysis of a thawed karyoplast after 2 h at room temperature. FIG. 2J, Spindle birefringence after transfer of a thawed karyoplast into an enucleated oocyte. FIG. 2K, Karyotype of stem cell line derived from a cryopreserved karyoplast, swaPS4, at passage 4. See Example 1.

FIGS. 3A-3I. Low levels of mtDNA carryover. FIG. 3A, Volume (black) and mtDNA copies (red) of karyoplasts and oocytes. Blue bar=mean. FIG. 3B, Distribution of mitochondria in the oocyte and FIG. 3C, the karyoplast. Size bar: 5 μm. FIG. 3D, Mean heteroplasmy quantification via ARMS-qPCR. Horizontal line indicates limit of detection. Error bars indicate standard deviation with mean value and n number displayed. FIG. 3E, RFLP analysis of swaPS1 and 2 at passages 2, 9 and as β-cells. U.C.=undigested control, Ud.=Undetectable. FIG. 3F, Heteroplasmy in swaPS3. ARMS-qPCR (gray) and RFLP (black); lines indicate limit of detection limits. FIG. 3G, FIG. 3H, FIG. 3I Directed differentiation into β-cells, neurons and fibroblasts. Scale bars: 50 μm. See Example 1.

FIG. 4A, Nanostring gene expression analysis of swaPS1 derived fibroblasts. mRNA counts per 100 ng RNA. FIG. 4B, Activities of mitochondrial respiratory complexes in ES, pES, and iPS cell lines derived from oocyte donor skin cells. FIG. 4C, Activities of mitochondrial respiratory complexes in swaPS1 and swaPS2 fibroblasts compared to control fibroblasts. FIG. 4D, Analysis of basal oxygen consumption rate (OCR) in swaPS1 and swaPS2 fibroblasts compared to control fibroblasts. Error bars in all panels indicate standard deviation. See Example 1.

FIG. 6A, Oocytes are obtained from two egg donors. White and dark gray circles/dots indicate mitochondria of different genotypes. After successful exchange, the oocyte contains mitochondria and cytoplasm from oocyte donor 2, and the nuclear genome from oocyte donor 1. A reciprocal exchange is also conducted. FIG. 6B, Artificial activation and development. Stem cells and various cell types are generated to determine the extent of heteroplasmy at different developmental stages.

FIGS. 7A-7T. (May also be referred to as supplementary FIGS. 2A-2K). Parthenogenesis and stem cell lines. FIG. 7A, Polar body (PB) extrusion and pronucleus (PN) formation upon artificial activation of parthenotes. FIG. 7B, Development to the blastocyst stage. FIG. 7C, Propidium iodide staining and flow cytometry analysis of pES3 at passage 4. The peak in window 1 are diploid cells at G1, the peak in window 2 are cells in S/G2 and M phase. Haploid cells were not detected. FIG. 7D, FIG. 7E, FIG. 7F, FIG. 7G, FIG. 7H, FIG. 7I, FIG. 7J, FIG. 7K and FIG. 7L, Pluripotency marker expression of parthenogenetic stem cell lines pES2, 3, 4 and 5. FIG. 7M, FIG. 7N and FIG. 7O, Teratoma analysis of pES2. FIG. 7P, State of heterozygosity determined by Affymetrix SNP genotyping. A value of 0 represents heterozygosity; a value of 1 represents homozygosity. FIG. 7Q, FIG. 7R, FIG. 7S and FIG. 7T, Karyotypes of parthenogenetic ES cell lines.

FIGS. 8A-8X. (May also be referred to as supplementary FIGS. 3A-3I). Development and Pluripotency. FIG. 8A, Two karyoplasts in the enucleation pipette and an enucleated oocyte. FIG. 8B, FIG. 8C, FIG. 8D, FIG. 8E, FIG. 8F, FIG. 8G and FIG. 8H, Development and blastocysts generation. FIG. 8F, FIG. 8G, Blastocysts generated using Sendai-mediated karyoplast fusion. FIG. 8H, Blastocyst generated using electrofusion. FIG. 8I, FIG. 8J, FIG. K, FIG. L, FIG. M, FIG. N, FIG. O, FIG. P and FIG. Q, Immunostaining of the swaPS1-3 cell lines. FIG. 8R, FIG. 8S and FIG. 8T, Teratoma formation from swaPS1 displaying tissues representative of each germ layer. Retinal pigment epithelium (RPE) and muscle are indicated by black and white arrows respectively. FIG. 8U and FIG. 8V, Karyotypes of swaPS2 and swaPS3. FIG. 8W, Nanostring gene expression analysis of swaPS cell lines. FIG. 8X, Mean number of CNVs specific to each cell line. Error bars represent standard deviation. N.S.=no significant difference.

FIG. 9B, Shown are the heterozygosity states for the X chromosome of somatic cells of the oocyte donors (ID 1110, 1111, 1115), as well as of parthenotes at various stages of development after genome exchange. Note the loss of heterozygosity (LOH) throughout the chromosome. 0 represents heterozygosity, 1 represents homozygosity. FIG. 9C, FIG. 9D, Array analysis of polar bodies. FIG. 9E, Array analysis of a parthenote. L (loss), N (normal) and G (gain). LOH, loss of heterozygosity.

FIGS. 10A-10G. (May also be referred to as supplementary FIG. 5). Enucleation and transfer of an immature spindle results in normal polar body Extrusion FIG. 10A, Removal of an immature spindle chromosome complex. S marks the immature spindle, MB marks the still attached mid-body. FIG. 10B, Spindle visualized by microtubule birefringence following karyoplast fusion by electrical pulse. FIG. 10C, FIG. 10D and FIG. 10E, Immunocytochemistry for markers of pluripotency upon stem cell derivation. FIG. 10F, Karyotype 46,XX. FIG. 10G, Heterozygosity (top) and copy number (below). 0 represents heterozygosity and 1 represents homozygosity. Note the loss of heterozygosity (LOH). The horizontal line indicates a copy number of 2.

FIG. 11O, Development to a small blastocyst with low cell count. Scale bar: 25 µm.

FIG. 12A, m.4715A is digested by BspEI into fragments (204 bp and 101 bp), whereas m.4715G sequence lacks the BspEI recognition site. FIG. 12B, m.16129A is digested by BanI into 2 fragments (176 bp and 211 bp), whereas m.16129G mtDNA has an additional BanI recognition site yielding 3 fragments (176 bp, 130 bp, and 81 bp). FIG. 12C, m.1670T sequence is digested by AluI into 2 fragments (120 bp and 192 bp), whereas m.1670A has an additional AluI recognition site yielding 3 fragments (120 bp, 60 bp, and 132 bp). FIG. 12D, Northern blot showing normal steady-state levels of mt-tRNAVal in skin derived fibroblasts of oocyte donor 1111, compared to controls. Values normalized to mt tRNALeu (UUR) and expressed as ratio. C1-5, controls. FIG. 12E, FIG. 12F, RFLP gels assessing the m.4715A/G variants showing no heteroplasmy was detected at any passage in swaPS1 (S1) or swaPS2 (S2).

FIG. 12G, FIG. 12H, RFLP gels assessing the m.16129A/G variants showing FIG. 12H, FIG. 12I and FIG. 12J, Low levels were detected in swaPS3 at low passage (P4-10) becoming undetectable at P13-14-20. FIG. 12K, FIG. 12L, Additional RFLP gels assessing the m.1670A/T variants showing no heteroplasmy was detected at any passage donors.

FIGS. 13A-13G. (May also be referred to as supplementary FIGS. 8A-8X). ARMS-qPCR Heteroplasmy analysis FIG. 13A, FIG. 13B, FIG. 13C and FIG. 13D, Confirmation of specificity of primers for 1110 and 1111 ARMS-qPCR and plots of expected heteroplasmy against measured heteroplasmy from ARMS-qPCR analysis for each swapped pair. FIG. 13E, Heteroplasmy in samples collected at preimplantation stage of development. (DPA=Day post activation). FIG. 13F, Heteroplasmy in individual swaPS lines at different passages and after clonal analysis. (P=Passage number).

FIG. 13G, Heteroplasmy in differentiated cells from swaPS cell lines. (SW1=swaPS1, SW2=swaPS2, SW4=swaPS4). In all cases horizontal line indicates limit of detection. 1110, 1111, 1114, 1115, 1126 and 1127 are oocyte donors.

FIGS. 14A-14K. (May also be referred to as supplementary FIGS. 9A-9E). Generation of swaPS-derived Fibroblasts, iPS Cells and Bottleneck Analysis FIG. 14A, Gating hierarchy used for selection of swaPS1-derived fibroblasts by FACS. CD13+ cells mark the fibroblast positive cells, with no TRA-1-60+/SSEA4+(stem cells) present. FIG. 14B, swaPS1-fibs could not spontaneously form stem cell colonies when grown in stem-cell conditions for 21 days. Scale bar represents 25 µm. FIG. 14C, Flow cytometry analysis further revealed the absence of TRA-1-60+/SSEA4+ cells. FIG. 14D, Gating hierarchy used for FACS selection of iPS cells following Sendai reprogramming showing the presence of TRA-1-60+/SSEA4+ cells. FIG. 14E, FIG. 14F and FIG. 14G, Pluripotency marker staining of swiPS1A, S1111A and 51110C2 cell lines. Scale bar represents 50 µm. FIG. 14H, Nanostring gene expression analysis of swiPS1A-F cell lines and iPS lines derived from oocyte donor fibroblasts (S1111A, S1111B, S1110C2). FIG. 14I, Heteroplasmy analysis of each swiPS clone and swiPS cell line. Heteroplasmy remained below the limit of detection (indicated by red line) for all clones. FIG. 14J, FIG. 14K, PCR detection of heteroplasmy after second round of amplification. j, 1111 could be detected in 1110 DNA at 0.0001% whilst 1110 could only be detected at 0.1% in 1111 DNA. k, swaPS1 showed no heteroplasmy at any passage (P), whilst swaPS2 was only positive at passage 2. swaPS3 was present until passage 10 after which point it was not detected. 1110 and 1111 are oocyte donors.

DETAILED DESCRIPTION OF THE INVENTION

Figure 4A:
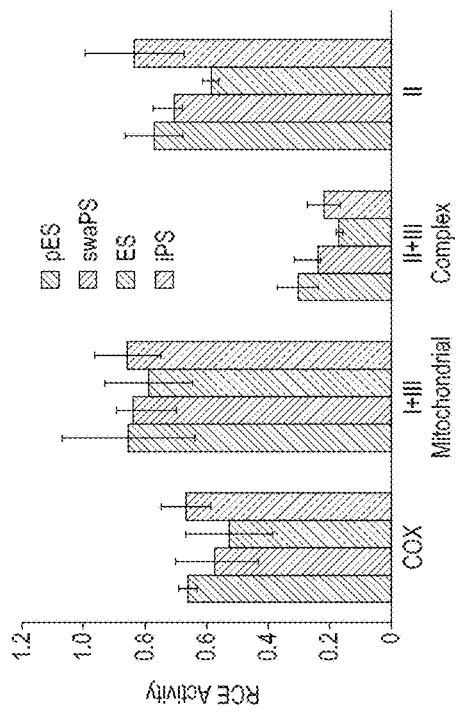
FIGS. 4A-4D. swaPS cells support a normal metabolic profile.

Many of the embodiments of the present invention are described in the above Summary of the Invention section of this application, as well as in the Examples, Drawings, and Claims. This Detailed Description section provides additional description relating to the various aspects of the invention, and is intended to be read in conjunction with the other sections of the present application.

The present invention provides modified oocytes having a nuclear genome derived from an oocyte of one female (a first oocyte), and cytoplasm derived from an oocyte obtained from a different female (a second oocyte), and methods for making and using such modified oocytes. The methods, compositions, and modified oocytes of the present invention can be useful in a variety of settings, as described herein. For example, data presented in Example 1 shows that the nuclear transfer methods described herein can be used to prevent transmission of mitochondrial DNA mutations in humans. Data presented in Example 2 shows that transfer of nuclear genomes from "aged" oocytes to enucleated "younger" oocytes, using the methods described herein, can result in the "aged" nuclear genomes adopting the developmental potential of the "younger" oocytes—providing proof-of-principle for the using the nuclear transfer methods of the present invention to improve oocyte competence and fertility.

Oocytes

The methods of the invention can be used with oocytes of various animal species. In some embodiments the present invention provides methods for use with oocytes from any mammalian species. In some embodiments, the methods of the invention can utilize rodent oocytes, such as mouse oocytes. In other embodiments the methods of the invention can utilize primate oocytes, such as human oocytes or oocytes from a non-human primate species. In some embodiments the oocyte from which the nuclear genome is obtained, and the enucleated oocyte into which the nuclear genome is transferred, should be from animals of the same species.

Oocytes for use in the methods of the present invention can be obtained and handled using suitable methods known the art—including any suitable veterinary or clinical methods. For example, methods of obtaining and handling human oocytes are well known in the art and are routinely used, for example, in fertility clinics when obtaining and handling human oocytes from patients for use in in vitro fertilization (IVF) techniques and other assisted reproduction techniques. Methods and instruments for micromanipulating oocytes, nuclei, karyoplasts and the like are well known in the art. Micropipettes and needles suitable for micromanipulation include, but are not limited to, those available Origio, Humagen, Cook Medica, and Eppendorf. Micropipettes can also be laboratory-made using a needle puller and a micro-forge. Any suitable micromanipulator for manipulating the micropipettes can be used, such as those available from Narishige, Sutter Instruments, Eppendorf and other manufacturers. Manipulations of oocytes, nuclei, karyoplasts and the like can be performed using a microscope, such as an inverted microscope having a heated stage and equipped with any required micromanipulators. Suitable microscopes include, but are not limited to, the NikonTE2000-U equipped with a 40× objective and Hoffman contrast optics, and the Olympus IX71 with relief contrast optics. Other exemplary methods for obtaining and manipulating oocytes are provided in Example 1 of the present application and/or are known in the art.

In some embodiments of the present invention an oocyte from which it is intended to remove the nuclear genome for subsequent transfer into an enucleated oocyte (often referred to as a "first" oocyte herein) is a developmentally incompetent oocyte. As used herein "developmental competence" refers to the capability of an oocyte to be fertilized, and/or to thereafter result in the generation of a zygote, generation of an embryo, implantation of an embryo, generation of a fetus, or birth of live offspring. A "developmentally competent" oocyte is one that is capable of, or expected to be capable of, successfully achieving, or leading to, the listed steps from fertilization through to at least the production of an embryo. A "developmentally incompetent" oocyte is one that is either not capable of, or is believed to be incapable of, successfully achieving, or leading to, one or more of the listed steps from fertilization through to birth of live offspring—whether through natural sexual intercourse or through any assisted reproduction method, such as in vitro fertilization. Thus, as used herein the phrase "developmentally incompetent oocyte" includes oocytes that have, or are believed to have, a reduced capability of maturing to the metaphase II stage, a reduced capability of being successfully fertilized, or that, if fertilized, have a reduced capability resulting in the generation of a zygote, embryo, fetus, or live offspring. The phrase "developmentally incompetent oocyte" also includes oocytes that may be capable of being successfully fertilized, generating a zygote, embryo, fetus, or live offspring, but that produce (or are likely to produce) zygotes, embryos, fetuses, or live offspring that have significant abnormalities, such as karyotypic abnormalities and the like. For example, a developmentally incompetent oocyte may be one that has, or is expected to have, a rate of fertilization, zygote generation, embryo formation, or viable fetus formation that is suboptimal, or lower than average, or significantly lower than average, and that may result in a failure to achieve, or reduced rate of achieving, pregnancy—whether naturally or through use of assisted reproduction techniques. Developmental incompetence of an oocyte may be associated with one or more of a variety of factors including, but not limited to, advanced maternal age, an oocyte cytoplasmic defect or deficiency, excessive time in vitro without fertilization, immaturity, cryopreservation, and the like.

In some embodiments the "first" oocyte from which the nuclear genome is obtained, has been in vitro for an excessive period of time without being fertilized. The developmental competence of oocytes declines when they remain unfertilized for prolonged periods in vitro. In humans the optimal time of fertilization is within less than 12 hours after ovulation or oocyte retrieval. Thus, in some embodiments of the present invention the oocyte may be one that is in vitro but has not been successfully fertilized within 10 hours after ovulation or retrieval of the oocyte from the subject. Such embodiments are particularly useful as they allow a means for rescuing oocytes that failed to become fertilized during an initial IVF cycle.

In some embodiments of the present invention a "first" oocyte, from which it is intended to remove the nuclear genome for subsequent transfer into an enucleated "second" oocyte, is obtained from a subject that is older (such as older than 30, 35, 40, 45, 50 or more years old in the case of human subjects), or from a subject that is infertile or has reduced or suboptimal fertility (such as infertility or reduced fertility associated with a defect or deficiency in one or more cytoplasmic factors), or from a subject that has had problems achieving fertilization, embryo development, implantation or pregnancy—either naturally and/or using one or more assisted reproduction methods (such as IVF).

In some embodiments of the present invention a "first" oocyte from which it is intended to remove the nuclear genome for subsequent transfer into an enucleated oocyte is an oocyte that has one or more mitochondrial defects or mutations and/or is obtained from a subject that has a mitochondrial defect, mitochondrial DNA mutation or mitochondrial disease. For example, in some such embodiments the nuclear genome is obtained from an oocyte of a subject having a disease that is associated with a mitochondrial DNA mutation—such as, but not limited to, Kearns Sayre syndrome, Leber's hereditary optic neuropathy or myoclonic epilepsy.

In some embodiments of the present invention an oocyte that is intended to be enucleated to form a cytoplast (often referred to as a "second" oocyte herein), such that the enucleated oocyte/cytoplast can then serve as a recipient of a nuclear genome from a "first" oocyte, is a developmentally competent oocyte and/or is obtained from a subject that is younger (such as less than 35, 30, 25, or 20 years old in the case of human subjects, or even younger), or from a subject that is fertile, or from a subject that has achieved successful fertilization, embryo development, implantation or pregnancy—either naturally and/or using one or more assisted reproduction methods (such as IVF).

In some embodiments of the present invention a "second" oocyte (i.e., an oocyte that is intended to be enucleated to form a cytoplast so that the cytoplast can then serve as a recipient of a nuclear genome from a first oocyte), is an oocyte that does not have one or more mitochondrial defects or mutations (such as defects or mutations that are known to be associated with disease) and/or is obtained from a subject that does not have one or more mitochondrial defects, mitochondrial mutations or mitochondrial diseases.

In some embodiments the oocytes used in the claimed methods are obtained from a subject at some desirable time point in the developmental cycle, such as at some desirable time point either before or after ovulation, or at a specific stage of oocyte maturation. In some embodiments the claimed methods may be used in conjunction with medical and/or veterinary treatments used to synchronize and/or stimulate ovulation. When human oocytes are used they may be obtained from a subject following treatment of the subject with a hormone or other drug used to stimulate ovulation, such as human chorionic gonadotropin ("hCG"). In some embodiments the oocytes are obtained from a human subject 30 to 40 hours after administration of an ovulation stimulus, such as hCG or leuprolide acetate, to the subject. In some embodiments the oocytes are obtained from a human subject less than 36 hours after administration of an ovulation stimulus, or 35 hours after administration of an ovulation stimulus, or less than 35 hours after administration of an ovulation stimulus.

In some embodiments of the present invention the "first" oocyte from which the nuclear genome is obtained, the "second" oocyte that is enucleated to form a cytoplast, or both the "first" and "second" oocytes, may have been cryopreserved prior to use. Similarly, in some embodiments the donor nuclear genome used in the claimed methods may have been previously cryopreserved (for example as a karyoplast within the zona pellucida of an oocyte or a small artificially formed karyoplast container, such as a plastic vessel) and/or the enucleated oocyte from which the cytoplasm is obtained, may have been previously cryopreserved (for example in the form of a cytoplast). In alternative embodiments fresh (i.e., not previously cryopreserved) oocytes, nuclear genomes, karyoplasts, enucleated oocytes and/or cytoplasts may be used in the methods of the invention. When frozen oocytes, nuclear genomes, karyoplasts, enucleated oocytes and/or cytoplasts are used any suitable freezing (cryopreservation) method known in the art may be used. For example, cryopreservation techniques are routinely used in fertility clinics to preserve and/or bank human oocytes for use in IVF procedures, and such methods can be used in conjunction with the present invention.

Nuclear Genomes to be Transferred

The nuclear genome of an oocyte comprises nuclear DNA, for example in the form of chromosomes, such as metaphase chromosomes. The nuclear genome may be within a "karyoplast" that comprises the nuclear DNA and a small amount of cytoplasm surrounded by a membrane, such as nuclear membrane and/or cell membrane. The nuclear genome may be without a surrounding membrane, and without cytoplasm.

In some embodiments a nuclear genome for use in the methods of the invention (i.e., to be transferred into a cytoplast) is obtained from an oocyte that is at some particular phase of its development and/or at some particular phase of the meiotic cycle. For example, in one embodiment the nuclear genome is obtained from a germinal vesicle nucleus. In another embodiment the nuclear genome is obtained from a metaphase I oocyte. In another embodiment the nuclear genome is obtained from an immature metaphase II oocyte, or before assembly of a mature metaphase II spindle. In another embodiment the nuclear genome is obtained from a mature metaphase II oocyte.

It is a finding of the present invention that transfer of a nuclear genome to an enucleated oocyte can be achieved more efficiently, and can lead to improved developmental competence of a resultant modified oocyte, when the nuclear genome is obtained/used before the mature metaphase II stage (for example at the immature metaphase II stage). For example, in some embodiments it may be preferable to obtain a nuclear genome from a "first" oocyte before formation of a mature metaphase II meiotic spindle during, for example, by obtaining the nuclear genome from an immature metaphase II oocyte within 2 hours after extrusion of the first polar body or before complete assembly of the metaphase II spindle. In other embodiments it may be preferable to obtain a nuclear genome from a mature metaphase II oocyte but to then treat the oocyte to induce partial spindle de-polymerization, for example using cryopreservation and/or by maintaining the mature metaphase II oocyte at room temperature for some period of time, such as up to 4 hours, or up to 2 hours, or from 1-2 hours, or by applying a microtubule depolymerizing drug, such as nocodazole, or vinblastine. Such methods differ from the nuclear used by others. For example, the nuclear transfer methods described in Mitalipov U.S. Patent Application US/2012/0036591 involve using mature metaphase II oocytes. Example 1 of the present application provides further details and experimental data relating to the effects of obtaining nuclear genomes from oocytes at different stages of the meiotic cycle or from oocytes having different degrees of formation/polymerization of their metaphase II meiotic spindle.

The nuclear genome from a "first" oocyte may be physically removed/obtained using standard methods known in the art for nuclear manipulation and nuclear transfer. For example, a nuclear genome may be obtained from a "first" oocyte with the assistance of visual methods such as contrast optics. In immature MII oocytes, the nuclear genome is attached to the polar body and may be removed by removing the first polar body. The removal of the genome may be assisted by using microtubule birefringence, or a non-toxic dye staining the chromosomes. Other methods that may be used to physically remove/obtain a nuclear genome from a "first" oocyte are provided in Example 1 of the present application and/or are known in the art.

Preparation of Enucleated Oocytes

In some embodiments an enucleated oocyte for use in the methods of the invention is obtained, or enucleated, when it is at some particular phase of its development and/or at some particular phase of the meiotic cycle. For example, in one embodiment the enucleated oocyte is obtained from a metaphase I (MI) oocyte. In another embodiment the enucleated oocyte is obtained from an immature MI oocyte, before or during spindle assembly. In another embodiment, the enucleated oocyte is obtained after arresting the oocyte at metaphase I using nocodazole, or another spindle depolymerizing agent. In another embodiment the enucleated oocyte is obtained from an immature metaphase II oocyte. In another embodiment the enucleated oocyte is obtained from a mature metaphase II oocyte. In some embodiments the enucleated oocyte is obtained before formation of a mature meiotic spindle during metaphase II, for example, by enucleating a recipient oocyte from an immature metaphase II oocyte within 2 hours after extrusion of the first polar body or before complete assembly of the metaphase II spindle. In another embodiment the enucleated recipient oocyte is obtained from a mature metaphase II oocyte that has been treated to induce spindle de-polymerization, for example using cryopreservation and/or by maintaining the mature metaphase II oocyte at room temperature for some period of time, such as up to 4 hours, or has been treated with nocodazole or another spindle depolymerizing agent.

The nuclear genome from a "second" oocyte may be physically removed using standard methods known in the art for nuclear manipulation and nuclear transfer. For example, the removal of the genome from a "second" oocyte to form an enucleated cytoplast may be performed with the assistance of visual methods, such as contrast optics. In immature MII oocytes, the nuclear genome is attached to the polar body and may be removed by removing the first polar body. The removal of the genome may be assisted by using microtubule birefringence, or a non-toxic dye staining the chromosomes. Other methods that may be used to enucleate a "second" oocyte are provided in Example 1 of the present application and/or are known in the art.

Transfer of Nuclear Genomes into Enucleated Oocytes

In embodiments that comprise introducing a nuclear genome from a first oocyte into an enucleated second oocyte (cytoplast), the step of "introducing" the nuclear genome can be facilitated using any suitable means known in the art.

One suitable method involves using an electrical pulse to fuse a donor nuclear genome (typically comprised in a karyoplast) with a recipient oocyte. Another suitable method means involves using a fusogenic agent to fuse the donor nuclear genome (typically comprised in a karyoplast) with the recipient oocyte. In embodiments where a fusogenic agent is used exemplary fusogenic agents include, but are not limited to, a Sendai virus (such as an inactivated Sendai virus) and polyethylene glycol. The nuclear genome may also be microinjected directly into the enucleated oocyte (cytoplast) using a glass pipette, in a manner similar to that used for the injection of sperm genomes during ICSI procedures. For example, a nuclear genome may be microinjected under the zona pellucida of an enucleated oocyte. Other exemplary methods for performing the nuclear transfer step are provided in Example 1 of the present application and/or are known in the art.

Fertilization and Embryo Development

In some embodiments the methods of the present invention involve taking a modified oocyte formed by the transfer of a nuclear genome from a first oocyte into an enucleated second oocyte and fertilizing the modified oocyte. Such modified oocytes can be used in one or more assisted reproduction procedures—such as are known in the art. For example, in some embodiments a modified oocyte may be fertilized in vivo (for example after placement of the modified oocyte into a reproductive tract). In other embodiments the modified oocyte may be fertilized in vitro, such as using an IVF method. Where the sperm to be used in the IVF method are of sufficient quality and competence a standard IVF protocol may be used. Where the sperm to be used in the IVF methods are of suboptimal quality or are incompetent to some degree, the IVF method used may involve intracytoplasmic sperm injection (ICSI). ICSI may also be used with normal sperm to increase the chance of fertilization. In some embodiments, following fertilization of a modified oocyte a zygote is formed. In some embodiments the zygote is cultured to form an embryo, such as a 2-cell embryo, a 4-cell embryo, an 8-cell embryo, a morula, or a blastocyst. In some embodiments the embryo is subsequently inserted into a suitable region of the reproductive tract of a female subject (such as the fallopian tubes or uterus) with the hope that the embryo might implant, establish a pregnancy, and ultimately develop into a viable fetus and lead to the birth of live offspring. Typically the embryo will be inserted into the subject's reproductive tract when it is at the cleavage stage, or at the blastocyst stage, or between day 3 and day 6 after fertilization. The subject into whose reproductive tract the embryo is inserted may be the same subject from whom the nuclear genome of the oocyte was obtained or may be a different subject.

In some embodiments it may be desirable to parthenogenetically activate the modified oocytes produced as described herein—instead of fertilizing the modified oocytes. Methods for parthenogenetic activation of oocytes are known in the art and any such methods can be used in accordance with the present invention.

Methods of Treatment

In some embodiments the present invention provides methods of treatment involving use of the methods described herein and/or modified oocytes made using such methods.

For example, in one embodiment the present invention provides methods for treating infertility involving use of the methods described herein and/or modified oocytes made using such methods. In this context the term "treating" includes, but is not limited to, a range of outcomes such as: improving the developmental competence of an oocyte, improving the likelihood of fertilization of an oocyte, improving the likelihood of generation of a zygote or an embryo, improving the likelihood implantation of an embryo, improving the likelihood of generation of a fetus, improving the likelihood of birth of live offspring, reducing the risk of karyotypic abnormalities, and improving the likelihood of success of an assisted reproduction procedure, such as an IVF procedure. In some embodiments the degree of improvement or degree of reduction of risk may be any degree that a subject, or a medical or veterinary practitioner, or a regulatory agency such as the FDA, would deem sufficient to warrant treating a subject as described herein. Thus, even small degrees of improvement or risk reduction may be within the scope of the term "treatment." Degrees of improvement or risk reduction may be determined, for example, by performing studies to quantify improvements in outcomes—whether at the population level (for example looking at particular patient populations or sub-populations), or at the individual level (for example looking at changes in outcomes for a particular individual) Such studies may be designed and analyzed using standard statistical and epidemiological methods used for performing clinical studies. In some embodiments the treatment methods described herein may lead to an improvement in an outcome, or a reduction of risk, of about 1%, or about 5%, or about 10%, or about 15%, or about 20%, or about 25%, or about 30%, or about 40%, or about 50%, or about 60%, or about 70%, or about 80%, or about 90%, or more as compared non-treated or placebo-treated groups or individuals (i.e., controls). For example, in one illustrative non-limiting example a treatment method of the present invention may result in a 1% to 100% improvement in the likelihood of fertilization of an oocyte.

In another embodiment the present invention provides methods for treating a disease caused by or associated with a mitochondrial DNA mutation involving use of the methods described herein and/or modified oocytes made using such methods. In this context the term "treating" encompasses a range of outcomes including, but not limited to, preventing or reducing transmission of a mtDNA mutation from a mother to the mother's offspring, reducing the proportion of mutant, relative to total, mitochondrial DNA (mtDNA) (i.e., heteroplasmy) within an oocyte, and/or reducing the severity of a disease associated with a mitochondrial DNA mutation in the mother's offspring. In some embodiments the degree of reduction may be any degree that a subject, or a medical or veterinary practitioner, or a regulatory agency such as the FDA, would deem sufficient to warrant treating a subject as described herein. Thus, even small reductions may be within the scope of the term "treatment." Degrees of reduction may be determined, for example, by performing studies to quantify changes in outcomes—whether at the population level (for example looking at particular patient populations or sub-populations), or at the individual level (for example looking at changes in outcomes for a particular individual) Such studies may be designed and analyzed using standard statistical and epidemiological methods used for performing clinical studies. In some embodiments the treatment methods described herein may lead to reduction of one or more measures described above of about 1%, or about 5%, or about 10%, or about 15%, or about 20%, or about 25%, or about 30%, or about 40%, or about 50%, or about 60%, or about 70%, or about 80%, or about 90%, or more as compared non-treated or placebo-treated groups or individuals (i.e., controls). For example, in one illustrative non-limiting example, a treatment method of the present invention may result in a 1% to 100% reduction in the proportion of mutant, relative to total, mitochondrial DNA (mtDNA) within an oocyte.

Preparation of Stem Cells

In some embodiments of the present invention stem cells (such as embryonic stem or "ES" cells) can be obtained from embryos made using the nuclear transfer methods described herein. Methods for obtaining pluripotent stem cells, such as ES cells, from blastocyst stage embryos are known in the art, and any such suitable method may be used in accordance with the present invention. For example, in one embodiment the inner cell mass of an embryo may be isolated after approximately six to seven days of development, or once the embryo has reached the expanded blastocyst stage. Pluripotent stem cells can be generated from this inner cell mass, for example using methods known in the art. In some embodiments the inner cell mass of a blastocyst may be isolated using a laser. In some embodiments it may also be possible to obtain pluripotent stem cells without isolation of the inner cell mass, for example by plating an intact blastocyst in a dish. In some embodiments the inner cell mass of a blastocyst may be plated on a layer of suitable feeder cells, including, but not limited to, a feeder layer of mouse embryonic fibroblast cells. The feeder layer may also be composed of human cells, or any other suitable substrate that can support the growth of human pluripotent stem cells. Such substrates include, but are not limited to, Matrigel, UV/ozone treated plasticware, gelatin-coated plastic, and the like. Any culture medium suitable for culture of pluripotent stem cells may be used, and several such media are known in the art. For example, the culture medium may be composed of Knockout DMEM, 20% Knockout Serum Replacement, nonessential amino acids, 2.5% FBS, Glutamax, beta-mercaptoethanol, 10 ng/microliter bFGF, and antibiotic. The employed medium may also be a variation of this medium, for example without the 2.5% FBS, or with a higher or lower % of knockout serum replacement, or without antibiotic. The employed medium may also be any other suitable medium that supports the growth of human pluripotent stem cells in undifferentiated conditions, such as mTeSR (available from STEMCELL Technologies), or Nutristem (available from Stemgent), or ES medium, or any other suitable medium known in the art. Other exemplary methods for generating/obtaining pluripotent stem cells from a blastocyst, such as a blastocyst made according to the methods of the present invention, are provided in Example 1 of the present application and/or are known in the art.

Kits

In some embodiments the present invention provides kits for performing the methods described herein. Such kits may include one or more reagents useful in performing the methods described herein together with instructions for carrying out the methods.

Other aspects of the present invention are either described elsewhere in the present application (such as the Examples), or are well known in the art. For example, methods for obtaining oocytes from a subject, the tools and equipment for manipulating oocytes, cryopreservation methods, IVF methods, in vitro embryo culture methods, and methods for placement of embryos in a patient's reproductive tract are well known in the art and any such suitable methods known in the art can be used in conjunction with the methods and compositions of the present invention.

EXAMPLES

The present invention may be further described and illustrated by way of the following non-limiting examples. (Reference numbers in parentheses or in superscript refer to the numbered reference list that follows the Examples, and which contains full citations to the cited material.)

Example 1

Nuclear Genome Transfer Between Human Oocytes

Example 1 describes nuclear genome transfer between human oocytes and improved methods for performing such transfer based, in part, on controlling the timing of transfer in relation to the meiotic process and manipulating the degree of assembly of meiotic spindles prior to transfer. Example 1 also provides data showing that such nuclear transfer methods can be used to prevent the transmission of mitochondrial mutations present in the oocyte from which the nuclear genome originates. However, the methods described herein can also be used in various other applications, including, but not limited to, fertility-related applications (for example involving transfer of nuclear genomes from developmentally incompetent to developmentally competent oocytes) and applications related to avoiding transmission of conditions/phenotypes that may be caused by non-nuclear defects other than mitochondrial genome defects. Example 2 demonstrates the applicability of such nuclear transfer methods to fertility-related applications.

The work described in Example 1 was published by the inventor(s) of the present application and others in the journal Nature on Jan. 31, 2013 (see Nature, Vol. 493, pp. 632-637, and the associated Supplementary information published on-line) with a preceding on-line publication on Dec. 19, 2012. The entire contents of this publication (including the associated supplementary information, is hereby incorporated by reference).

Mitochondrial DNA mutations transmitted maternally within the oocyte cytoplasm often cause life-threatening disorders. Here we explore the use of nuclear genome transfer between unfertilized oocytes of two donors in order to prevent the transmission of mitochondrial mutations. Nuclear genome transfer did not reduce developmental efficiency to the blastocyst stage and genome integrity was maintained provided that spontaneous oocyte activation was voided through the transfer of incompletely assembled spindle-chromosome complexes. Mitochondrial DNA transferred with the nuclear genome was initially detected at levels below 1%, decreasing in blastocysts and stem cell lines to undetectable levels, and remained undetectable after passaging for over one year, clonal expansion, differentiation into neurons, cardiomyocytes or β-cells, and after cellular reprogramming. Stem cells and differentiated cells had mitochondrial respiratory chain enzyme activities and oxygen consumption rates indistinguishable from controls. These results demonstrate the potential of nuclear genome transfer in humans, for example to prevent the transmission of mitochondrial disorders and for other applications.

A critical determinant of the phenotypic severity in most maternally inherited mitochondrial diseases is heteroplasmy, i.e., the proportion of mutant, relative to total, mitochondrial DNA (mtDNA) within a cell. Due to the cytoplasmic segregation of mitochondria during cell division, the level of heteroplasmy is subject to broad fluctuations, in particular during the developmental expansion of mtDNA from the premeiotic germ cell to the mature human oocyte (1-4). As a result, an unaffected carrier of a mtDNA mutation may have an affected child. Whilst prenatal genetic diagnosis can select embryos with a reduced mutation load, variation between blastomeres in single embryos limits the effectiveness of such screening3, and significant levels of mutant mtDNA can remain resulting in a carrier (5).

Based on these considerations, the Nuffield Council on Bioethics has endorsed research to prevent transmission of mtDNA mutations (6), including the transfer of the nuclear genome into an enucleated oocyte containing normal mitochondria. In mice, transfer between fertilized eggs (zygotes) is effective in preventing the transmission of pathogenic mtDNA (7) and in rhesus monkeys, genome exchange between unfertilized oocytes gave rise to live births (8). In human cells, the transfer of pronuclei between zygotes resulted in minimal carryover of donor mtDNA (9). However, the exchange reduced developmental potential, possibly because the transfer introduced an abnormal centrosome number, resulting in multipolar spindles (10) and aneuploidy (11). Since the centrosome is sperm-derived (12), nuclear genome exchange prior to fertilization avoids this issue. Furthermore, pronuclear transfer requires the fertilization of both donor and recipient oocytes, resulting in the destruction of half of the embryos. In contrast, human oocytes would only be fertilized following successful genome exchange. Nuclear transfer between fertilized eggs may also lead to cell cycle asynchrony between the nucleus and the cytoplasm, and as a consequence, reduced developmental competence.

Figure 6A:
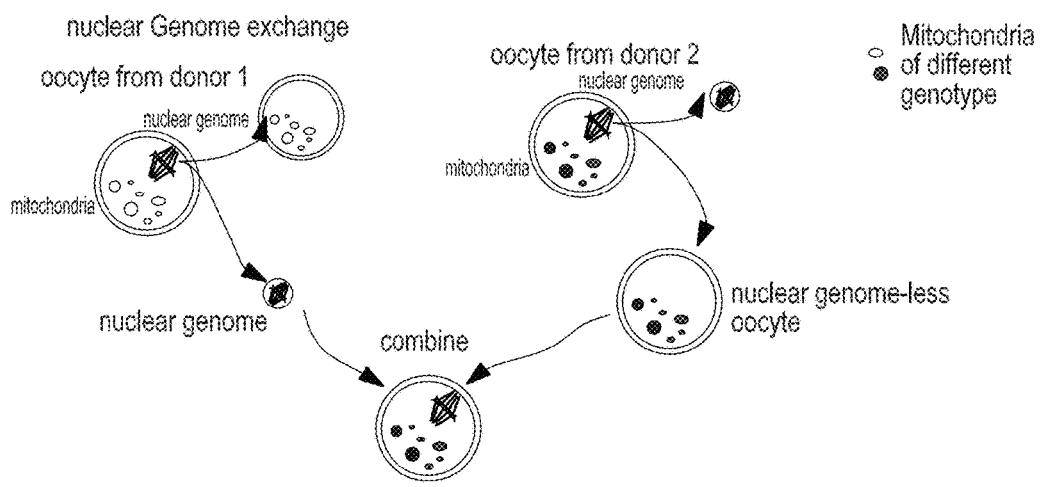
FIGS. 6A-6B. (May also be referred to as supplementary FIGS. 1A-1H). Genome exchange in human oocytes.
Figure 6B:
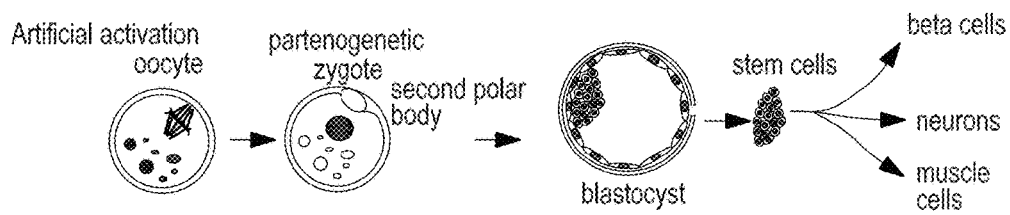

To determine the consequences of nuclear genome transfer in unfertilized oocytes, we chose parthenogenetic activation instead of fertilization, as it avoids the generation of human embryos for research (FIG. 6—also referred to as Supplementary FIG. 1). It also allows assessing damage to the nuclear genome, as development relies exclusively on the transferred genome, excluding the possibility of complementing these defects by the sperm genome that has not been manipulated. Transfer of the nuclear DNA (nDNA) between oocytes of two unrelated women resulted in the exchange of the mitochondrial genotype and the elimination of mtDNA variants, including a variant found in the MT-TV gene (encoding mt-tRNAVal). However, nuclear genome transfer frequently induced premature oocyte activation and failure to normally extrude the second polar body. As manipulation-induced karyotypic abnormalities present a risk beyond those normally incurred during assisted reproductive technologies, this is likely an obstacle to the clinical translation of this technique. We found that premature activation could be prevented by partial depolymerization of the spindle-chromosome complex through cryopreservation or cooling to room temperature, allowing normal polar body extrusion, efficient development to the blastocyst stage, and the derivation of karyotypically normal stem cells. Therefore, nuclear genome transfer, rather than the transfer of intact spindle-chromosome complexes should be effective in preventing the transmission of mtDNA mutations.

Efficient Development after Genome Exchange

We first determined that artificial activation of unfertilized oocytes resulted in extrusion of the second polar body (FIG. 7a—also referred to as Supplementary FIG. 2a) and efficient development to the blastocyst stage (FIG. 1a), allowing derivation of four stem cell lines (pES2-5; FIG. 7b-o—also referred to as Supplementary FIG. 2b-o). If polar body extrusion had accurately segregated sister chromatids, a haploid zygote with 23 chromosomes should result with stem cell lines devoid of heterozygosity. STR genotyping and Affymetrix single nucleotide polymorphism (SNP) arrays revealed that 4/4 stem cell lines were homozygous for all chromosomes (FIG. 7p—also referred to as Supplementary FIG. 2p). All cell lines were diploid (FIG. 7q-t—also referred to as Supplementary FIG. 2q-t), suggesting that the genome had undergone endoreplication, as previously observed in mouse parthenotes (13). These results suggest that parthenogenesis is appropriate for in vitro studies on the feasibility and consequences of oocyte genome exchange.

Figure 9A:
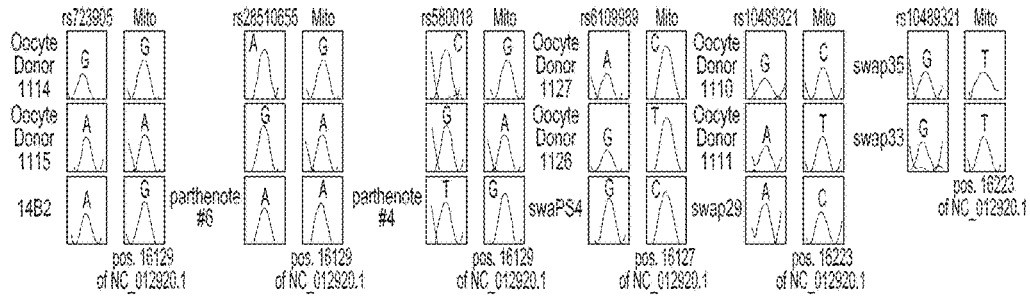
FIGS. 9A-9E. (May also be referred to as supplementary FIGS. 4A-4D). Polar body extrusion after nuclear genome exchange FIG. 9A, Sequencing of SNPs in nuclear and mitochondrial genome confirming the swap. rs number indicates nuclear genome SNP.
Figure 9B:
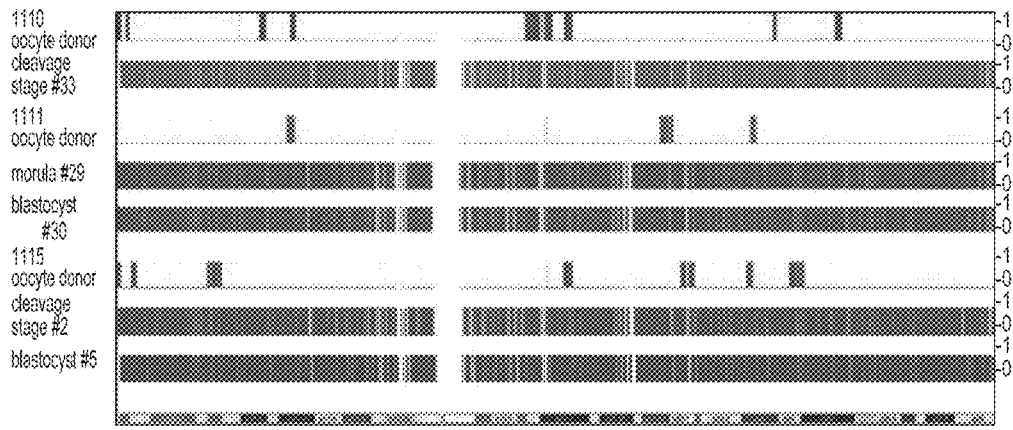
Figure 9C:
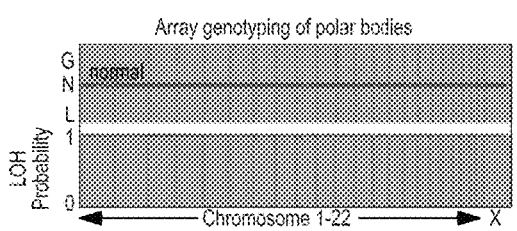
Figure 9D:
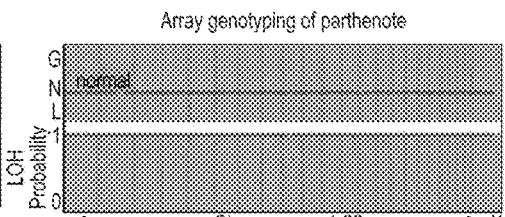
Figure 9E:
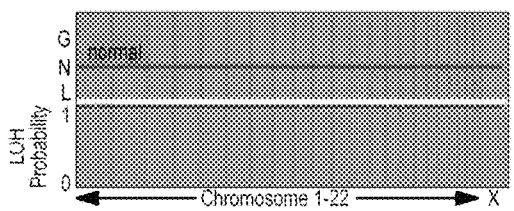

To exchange the nuclear genome between oocytes of two different donors, menstrual cycles were synchronized using oral contraceptives, with synchronized retrieval successful in all (4/4) women. Four oocyte donors donated a total of 62 mature metaphase II (MII) oocytes (19, 17, 11 and 15 oocytes for the individual donors). Using microtubule birefringence, 18 of these oocytes had the nuclear genome removed (FIG. 1b) and subsequently fused to enucleated oocytes using either Sendai virus or an electrical pulse. Development upon exchange was very efficient: of the 18 oocytes, 7 developed to the blastocyst stage, with at least one blastocyst for each donor (FIG. 1a-d, FIG. 8a-h—also referred to as Supplementary FIG. 3a-h). From these blastocysts, 3 swapped pluripotent stem cell lines (swaPS) were derived. SwaPS cells expressed markers of pluripotency, had gene expression profiles comparable to those of established embryonic stem (ES) and parthenogenic embryonic stem (pES) cell lines and were able to differentiate into cell types and tissues of each germ layer (FIG. 1e, FIG. 8i-t—also referred to as Supplementary FIG. 3i-t). Sequencing of mtDNA and nDNA (nDNA) polymorphisms and STR genotyping confirmed that nuclear genome transfer had resulted in the exchange of the mitochondrial genotype (FIG. 1f, FIG. 9a—also referred to as Supplementary FIG. 4a).

To determine whether the transfer affected the integrity of the nuclear genome, karyotype analysis and high-resolution SNP arrays were used. Both swaPS1 and swaPS2 had normal karyotypes of 46,XX chromosomes, while swaPS3 contained an additional chromosome 12 (FIG. 1g, FIG. 8u-v—also referred to as Supplementary FIG. 3u-v). The origin of this additional chromosome was due to a mitotic segregation error, as chromosome 12 did not contain regions of heterozygosity by SNP array analysis. Although trisomy 12 is a frequent artifact of in vitro stem cell culture14, karyotyping of swaPS1 after 9 months in culture revealed no alterations. Manipulation-induced strain on chromosomes during genome exchange might result in chromosome breaks and faulty repair, as no homologous template is available upon segregation of sister chromatids. Duplication during S-phase would result in a homozygous copy number change (CNVs). We identified an average of 3.75 homozygous CNVs in five cell lines with spindle transfer and 4.25 in four unmanipulated parthenogenetic stem cell lines (FIG. 1h). SwaPS4, and the unmanipulated cell line pES7, originate from the same donor and were found to share more than half of the CNVs, suggesting that most, if not all, CNVs originated in the female germline, and were not generated by the manipulation. We also found no differences in the number of heterozygous CNVs (FIG. 8x—also referred to as Supplementary FIG. 3x). To determine whether epigenetic alterations resulted in gene expression changes following genome transfer, gene expression in manipulated cell lines was compared to unmanipulated controls. Only 1 gene (THBS1—Thrombospondin 1) was significantly (p<0.01) downregulated with no genes significantly upregulated.

SwaPS2 and 3 were homozygous for 99.8% of the genome, consistent with accurate extrusion of a haploid genome into the polar body. The 0.2% of heterozygosity was due to copy number variants that diverged in sequence. In contrast, swaPS1 was homozygous for merely 43.3% of the genome (FIG. 2a), consistent with a cell line that had undergone the first, but not the second, meiosis (15). To determine the frequency of chromosome segregation errors during preimplantation stages, we biopsied polar bodies and blastomeres, or used morulas and blastocysts, for analysis. Using whole-genome amplification, followed by either PCR of loci on all 23 chromosomes or microarray-based analysis, we found that 7/9 preimplantation embryos were homozygous throughout the genome, demonstrating normal polar body extrusion (FIG. 9b-e—also referred to as Supplementary FIG. 4b-e). One was heterozygous for all chromosomes, while another showed a copy number gain and heterozygosity on chromosome 4, demonstrating that polar body extrusion had been inaccurate (FIG. 2b). Failed, or inaccurate extrusion of the polar body was likely due to the transfer procedure, as we did not observe any heterozygosity in unmanipulated stem cell lines (FIG. 7p—also referred to as Supplementary FIG. 2p) (16).

Immature Spindles Prevent Spontaneous Activation

Through transfer of karyoplasts into oocytes of either the same or a different donor, we determined that upon transfer using electrical pulses, all oocytes (13/13) formed one or two pronuclei 3-5 h post transfer, suggesting that the electrical pulse had caused premature exit from meiosis. Parthenotes with molecularly confirmed karyotypic abnormalities were all derived from oocytes that were activated as a result of the transfer. In contrast, none of the oocytes (0/14) fused to karyoplasts using Sendai virus activated as a result of the manipulation. All remained at meiosis for 4-6 h post transfer, and extruded a second polar body only upon artificial activation using a calcium ionophore followed by incubation in the translation inhibitor puromycin (FIG. 2c-d).

Figure 5:
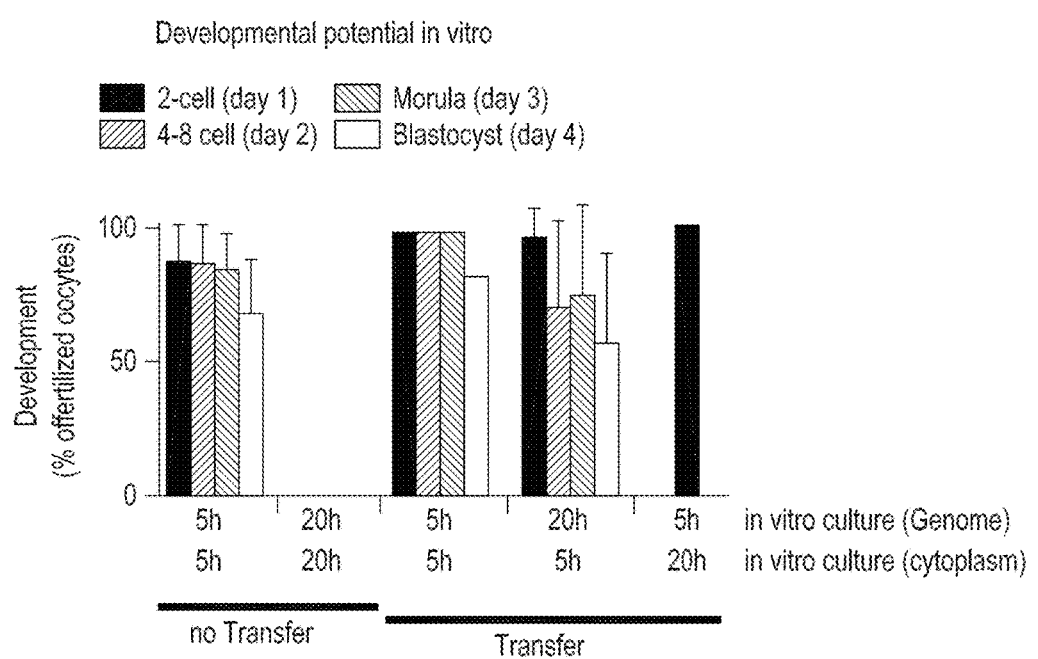
FIG. 5 is a graph showing the percentage of mouse embryos developing to the 2-cell, 4-8 cell, morula, and blastocyst stages under different nuclear genome transfer conditions. Note there is no development to the blastocyst stage when the cytoplasm is kept in culture for 20 hours post retrieval, but if a genome cultured for 20 h is transferred into cytoplasm that has been kept in culture for 5 hours post retrieval, efficient development to the blastocyst stage occurs. See Example 2.

We reasoned that manipulation-induced activation was related to the spindle-chromosome complex. When oocytes without a spindle were exposed to an identical electrical fusion pulse during somatic cell nuclear transfer, they remained stable in meiosis (16). Furthermore, when sperm is injected prematurely, within an hour after extrusion of the first polar body and prior to the assembly of a mature MII spindle, most oocytes fail to activate (17). This suggests that upon an activating stimulus, only mature spindles with bipolar attachment of chromosomes generate a signal promoting the exit from meiosis, thereby ensuring accurate chromosome segregation. To explore whether immature spindles prevented manipulation-induced activation, we monitored an oocyte progressing from metaphase I (MI) to MII and aspirated the nuclear genome within 1 h after extrusion of the first polar body, while the spindle was still immature (FIG. 10a—also referred to as Supplementary FIG. 5a). Transfer-induced activation did not occur and only upon artificial activation did the oocyte extrude the polar body and develop to the blastocyst stage, allowing derivation of a pluripotent stem cell line (pES6) with a normal karyotype and homozygosity across the genome (FIG. 10b-g—also referred to as Supplementary FIG. 5b-g).

Figure 11A:
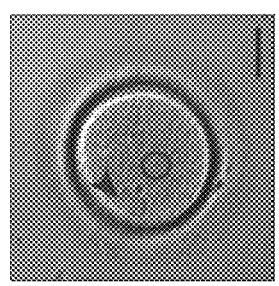
FIGS. 11A-11O. (May also be referred to as supplementary FIGS. 6A-6B). Cryopreservation of karyoplasts is compatible with normal polar body extrusion and preimplantation development FIG. 11A, Polar body extrusion (arrowhead) and formation of a single pronucleus (circled) upon transfer of a thawed karyoplast into an enucleated, fresh oocyte of a different donor.
Figure 11B:
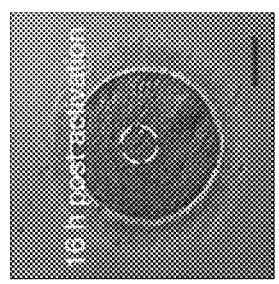
FIG. 11B, Pronuclear morphology on day 1 post activation.
Figure 11C:
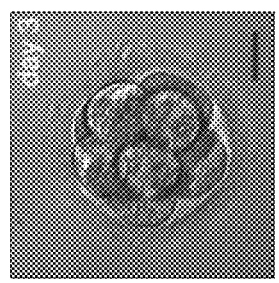
FIG. 11C, FIG. 11D, FIG. 11E and FIG. 11F, Developmental progression to the blastocyst stage. Time indicates the days post artificial activation.
Figure 11D:
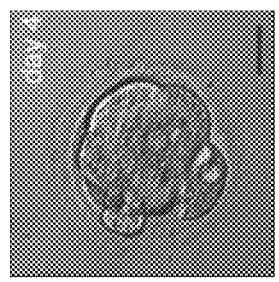
Figure 11E:
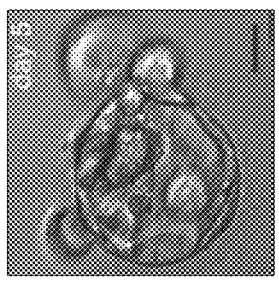
Figure 11F:
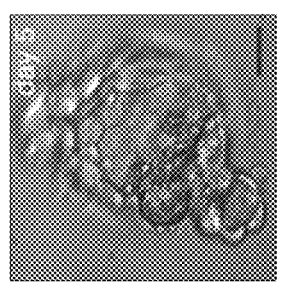
Figure 11G:
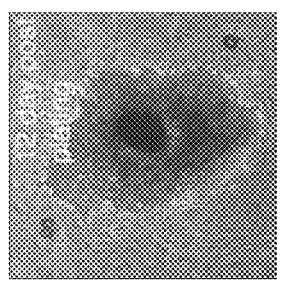
FIG. 11G, Stem cell outgrowth of swaPS4.
Figure 11H:
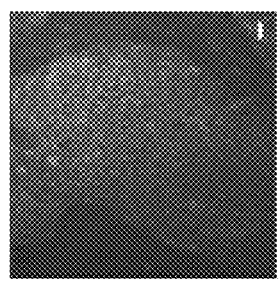
FIG. 11H, FIG. 11I and FIG. 11J, Pluripotency marker expression of swaPS4.
Figure 11I:
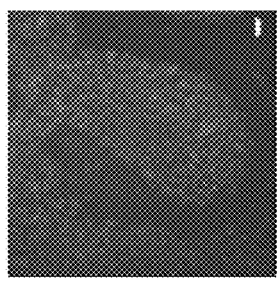
Figure 11J:
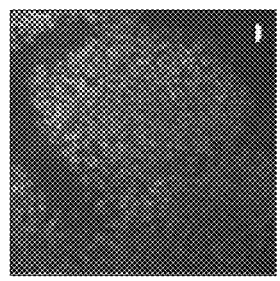
Figure 11K:
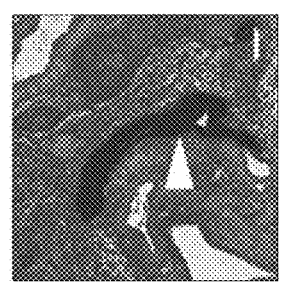
FIG. 11K, FIG. 11L, Teratoma analysis of swaPS4 showing tissues from each germ layer. Retinal pigmented epithelium (k) and muscle (l) are indicated by arrowheads.
Figure 11L:
Figure 11M:
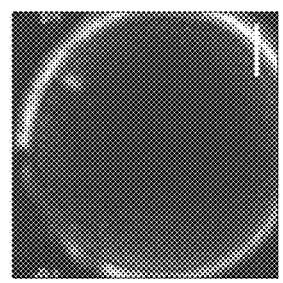
FIG. 11M, Transfer of a fresh (non-cryopreserved) karyoplast transfer into a thawed, enucleated, oocyte.
Figure 11N:
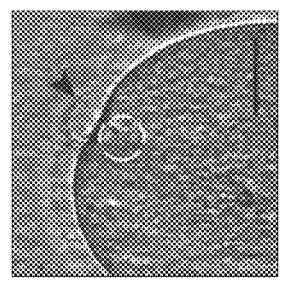
FIG. 11N, Polar body extrusion (arrowhead) and formation of a single pronucleus (circled). Activation occurred prematurely.
Figure 11O:
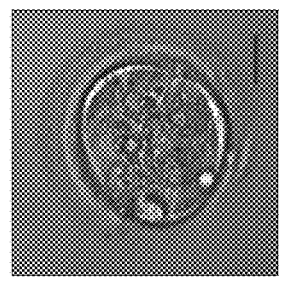
Figure 12A:
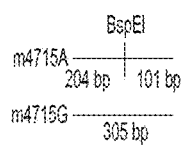
FIGS. 12A-12L. (May also be referred to as supplementary FIGS. 7A-7T). RFLP Heteroplasmy analysis FIG. 12A, FIG. 12B and FIG. 12C, Scheme of the RFLP designed using 3 different mtDNA variants.
Figure 12B:
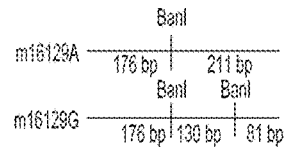
Figure 12C:
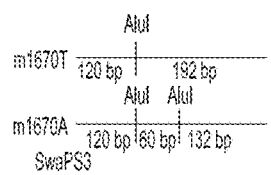
Figure 12D:
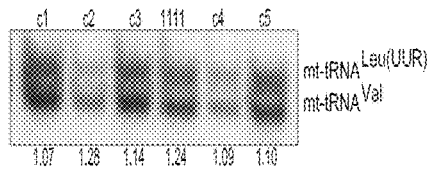
Figure 12E:
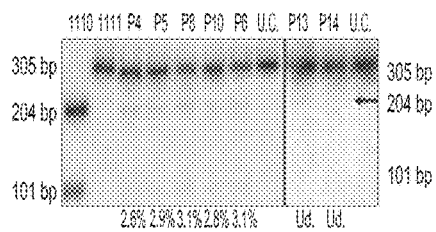
Figure 12F:
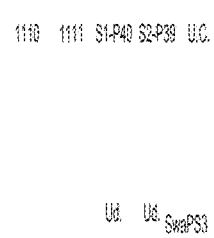
Figure 12G:
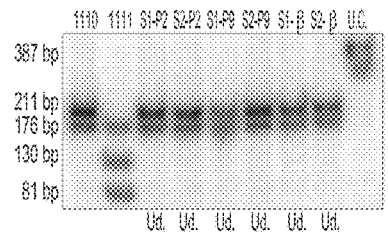
Figure 12H:
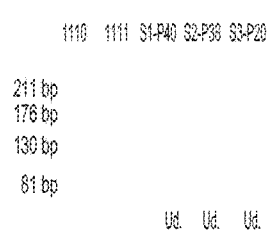
Figure 12I:
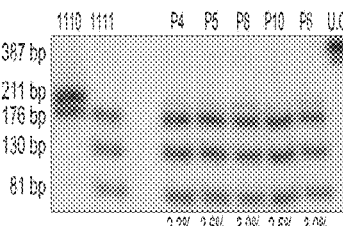
Figure 12J:
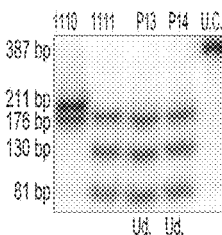
Figure 12K:
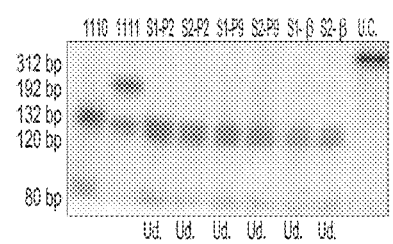
Figure 12L:
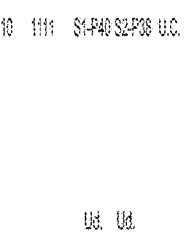

As timing the removal of the nuclear genome relative to the extrusion of the first polar body may not be practical in all circumstance, we used reduced temperatures to induce partial spindle depolymerization in mature MII oocytes. As the removal of the spindle-chromosome complex relies on the presence of a birefringent spindle, we extracted the nuclear genome on the heated stage of a microscope, before exposing the karyoplast to reduced temperatures. Two karyoplasts were placed on ice for 2 h, and then re-transferred by electrofusion into enucleated oocytes kept at 37° C. Fused oocytes remained in meiosis for more than 3 h post transfer and required an artificial activation stimulus for polar body extrusion. We next extracted karyoplasts from 30 oocytes and cryopreserved them below the zona pellucida of an immature oocyte (FIG. 2e). Upon thawing, 27/30 karyoplasts were intact. Spindle birefringence was not detected immediately after thaw but re-formed in karyoplasts kept at 37° C. for approximately 2 h (2/2), but not when maintained at room temperature (0/3) (FIG. 2f-h). Cryopreservation did not result in the dispersion of chromosomes: in all five karyoplasts, chromosomes remained attached to microtubules (FIG. 2i), consistent with the finding that some, but not all spindle microtubules are cold sensitive18. Within 1 h post thaw, three karyoplasts were fused to enucleated oocytes of a different donor using electrical pulses. At 4 h post transfer, we observed a birefringent spindle with perpendicular alignment to the oolemma (FIG. 2j). All (3/3) oocytes remained stable at meiosis and extruded the second polar body only upon artificial activation, forming a single pronucleus (FIG. 11a-b—also referred to as Supplementary FIG. 6a-b). Two of the three parthenotes (66%) developed to the blastocyst stage, allowing the derivation of the karyotypically normal stem cell line swaPS4 (FIG. 2k, FIG. 11c-l—also referred to as Supplementary FIG. 6c-l). Homozygosity throughout the genome showed that polar body extrusion had normally segregated sister chromatids (FIG. 2a). An additional thawed karyoplast was kept at 37° C. for 4 h, and only then fused to the oocyte, resulting in spontaneous activation and a failure to extrude the second polar body.

Furthermore, we vitrified MII oocytes. Immediately after thaw, birefringence of the microtubule spindle was undetectable in all oocytes (0/6). Following incubation for 1-2 h at 37° C., birefringence became visible in all 6 thawed oocytes, which were subsequently enucleated. Spindle-chromosome complexes from oocytes of a different donor retrieved on the day of thawing were transferred into 5 enucleated oocytes by electrofusion, with one karyoplast failing to fuse. One of the 5 oocytes developed to the blastocyst stage (FIG. 1a, FIG. 11m-o—also referred to as Supplementary FIG. 6m-o). Unlike in oocytes post-transfer of cryopreserved karyoplasts, all four oocytes, post-transfer of reconstituted spindle-chromosome complexes, underwent spontaneous activation during the relevant time period (FIG. 2d). These results demonstrate that the maturation of the spindle-chromosome complex plays a major role in the ability of human oocytes to exit meiosis.

Stable Exchange of Mitochondrial Genotypes

To determine mitochondrial genotypes, we identified polymorphic mtDNA variants (SNPs) in the hypervariable regions (HVRI and III) of each donor, and sequenced the complete mtDNA genome of two donors. Two polymorphisms, m.4715A>G (ND2), and m.16129A>G (non-coding region) were homoplasmic by restriction fragment length polymorphism (RFLP). Moreover, one of the donors was homoplasmic for a variant at the 3'-terminus of the MT-TV gene (m.1670A>T) that has been identified as a rare polymorphism (19). Whilst no differences in mt-tRNAVal steady-state level were observed in cultured fibroblasts, a functional significance is possible as an analogous 3'-terminus polymorphism in mt-tRNAGlu has been identified as a pathogenic mutation (20) (FIG. 12a-d—also referred to as Supplementary FIG. 7a-d).

To estimate the amount of potential mtDNA carryover, we quantified mtDNA in human oocytes and karyoplasts using quantitative PCR (qPCR). Karyoplasts had an average mtDNA copy number of 1129±785 (mean±s.d., n=22), or 0.36% of the total mtDNA found within MII oocytes (311,146±206,521, mean±s.d., n=5) (FIG. 3a). This corresponded with volumetric measurements of karyoplasts, which were 0.89% of that of intact oocytes (4961±1964 µm3 vs 559093±245,217 µm3, respectively; mean±s.d., n=18 and 21) (FIG. 3a). Staining of mitochondria in oocytes and karyoplasts with MitoTracker® or antibodies recognizing the complex V alpha subunit indicated that the spindle-chromosome complex was devoid of mitochondria (FIG. 3b-c). We therefore expected mtDNA carryover of less than 1%.

Heteroplasmy was determined by last-hot cycle PCR, with a detection threshold of approximately 2%, and allele refractory mutation system (ARMS)-qPCR, with a detection threshold of approximately 0.5% (FIGS. 12-13—also referred to as Supplementary FIGS. 7-8) (21,22). As significant fluctuations in heteroplasmy have been reported in blastomeres of mouse and monkey embryos (23,24), we first quantified 17 embryos at cleavage stage, including individual blastomeres, and found heteroplasmy to be <0.5%. In 7 samples that reached morula or blastocyst stage, the average heteroplasmy remained <0.5%, and in all cases 1% or lower. Overall, preimplantation embryos had a mean heteroplasmy of 0.31%±0.27% (mean±SD, n=24; FIG. 3d, FIG. 13e—also referred to as Supplementary FIG. 8e).

With the generation of stem cell lines, we asked whether the original mitochondrial genotype could re-emerge following extensive passaging, clonal expansion, cellular differentiation and reprogramming. Quantification at passages (P) 2 to 59 (one year in culture), showed that heteroplasmy in swaPS1, 2 and 4 remained undetectable (FIG. 3d-e, FIGS. 12e-l, 13f—also referred to as Supplementary FIGS. 7e-l, 8f). mtDNA heteroplasmy was detected at low levels in swaPS3 at P4-10 (2.79%±0.27%, mean±s.d.; range: 2.3-3.1% by RFLP), but became undetectable from passage 14 onward (FIG. 3f, FIG. 12e,i-j—also referred to as Supplementary FIG. 7e,i-j). As heterogeneity in heteroplasmy may not be detected by population analysis, 10 colonies for each swaPS cell line were grown from single cells. In all 40 colonies, heteroplasmy was undetectable (FIG. 3d, FIG. 13f—also referred to as Supplementary FIG. 8f).

In mice, specific mitochondrial genotypes can selectively expand in differentiated cells, resulting in altered levels of heteroplasmy (25,26). To determine whether such alterations occurred after differentiation, cells of each germ layer (pancreatic cells, neurons, fibroblasts and cardiomyocytes) were differentiated in vitro (FIG. 3g-i). Heteroplasmy was undetectable via either ARMS-qPCR or RFLP (FIG. 3d-e, FIG. 8g—also referred to as Supplementary FIG. 8g).

A bottleneck in the mitotic inheritance of mitochondrial DNA mutations occurs during induced pluripotent stem (iPS) cell generation, resulting in iPS cell colonies with differing percentages of a mitochondrial mutation (27). To test whether such a bottleneck (mimicking the one in the female germline) could alter the ratio of the two mitochondrial genotypes, we reprogrammed fibroblasts differentiated from swaPS cells (FIG. 4a) into iPS cells (FIG. 14a-h—also referred to as Supplementary FIG. 9a-h). In 43 iPS cell colonies and 6 cell lines, termed swiPS, heteroplasmy was undetectable (mean heteroplasmy 0.01%±0.04%; mean±s.d, n=43; FIG. 3d, FIG. 14i—also referred to as Supplementary FIG. 9i). As none of these manipulations resulted in re-emergence of significant levels of heteroplasmy, we next asked whether swaPS cells retained any mitochondrial DNA transferred with the karyoplast. Using repeat-PCR amplification of a product in the HVR, with 5 SNPs per primer pair, we could specifically amplify the minority product. In neither swaPS1 nor swaPS2 could the minority product be detected beyond passage 2 (detection limit 0.0001%), whilst in swaPS3 detection was seen until P18 after which it was undetectable (detection limit 0.1%; FIG. 14i-j—also referred to as Supplementary FIG. 9i-j). As stem cells and fibroblasts contain less than 1500 mtDNA copies (28), a significant proportion of the cell population must be homoplasmic.

Normal Mitochondrial Activity in swaPS Cells

Figure 4B:
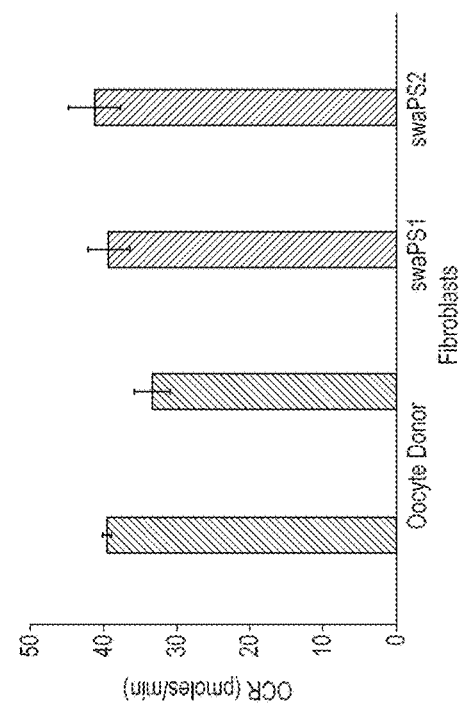
Figure 4C:
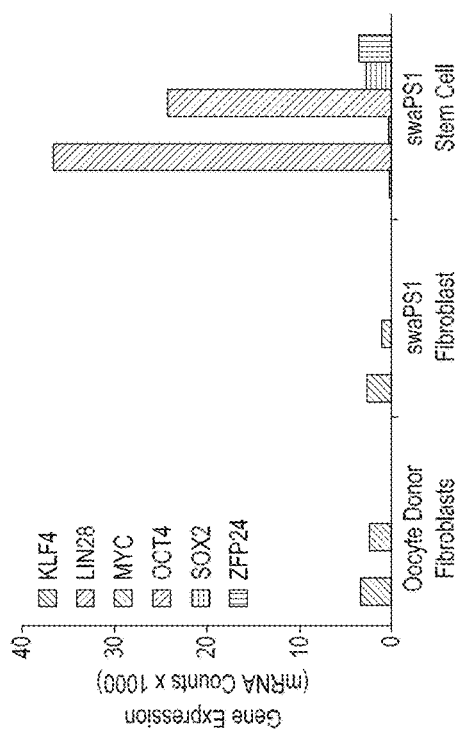
Figure 4D:
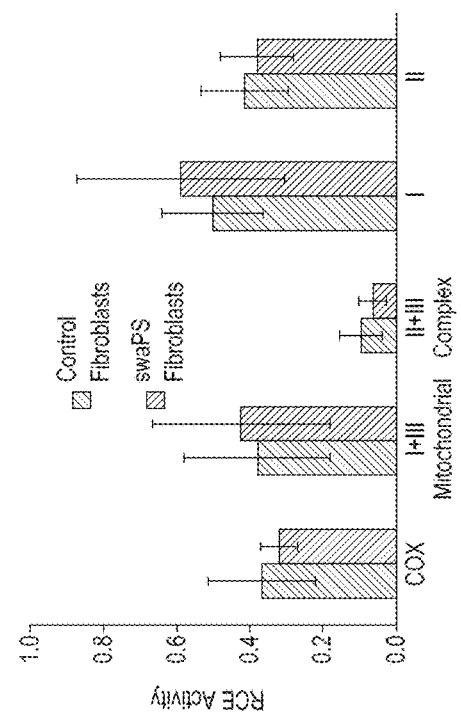

Despite the low levels of mitochondrial heteroplasmy, we considered the possibility that the presence of two mitochondrial genotypes within the same cell might impair mitochondrial functions (26). We determined that swaPS1 and swaPS2 had population doubling times of 33 and 31.5 h respectively a proliferation rate comparable to ES cell lines (29), suggesting no metabolic disadvantage as a result of the exchange. We next determined the biochemical activities of mitochondrial respiratory chain enzymes. No differences were found in comparisons between undifferentiated swaPS1 and swaPS2, ES, pES, and iPS cell lines generated from oocyte donor skin fibroblasts (FIG. 4b). We also assessed mitochondrial respiratory chain enzyme activities in differentiated cell types (FIG. 4c) and basal oxygen consumption in live culture (FIG. 4d), and found no differences between swaPS-fibroblasts and oocyte donor skin fibroblasts.

Discussion

Although much of the discussion here, and the data presented in this example, relates to the transfer of a nuclear genome from one oocyte to another to avoid inheritance of mitochondrial genome variants, the nuclear transfer methods described here can also be used in a variety of other settings, for example to transfer a nuclear genome from a first oocyte that has some other kind of defect or abnormality to a second oocyte that does not have that defect or abnormality. Such defects or abnormalities could include other cytoplasmic defects, reduced developmental competence, and the like. The present invention, including this Example, provides several improved techniques for nuclear transfer (for example based on the timing of the transfer in relation to the meiotic cycle and the based on the state of assembly of meiotic spindles) that can be useful for a wide variety of nuclear transfer applications. All of the nuclear transfer methods described herein can be used for any such applications, without limitation.

Here we show that the transfer of nuclear genomes into human oocytes results in efficient preimplantation development, with essentially complete and mitotically stable exchange of the mitochondrial lineage, supporting normal mitochondrial activity. The low levels of heteroplasmy that are detected immediately after transfer become undetectable and do not increase upon clonal expansion, cellular differentiation, or when exposed to a bottleneck. Any potentially remaining heteroplasmy is far below the levels required for clinical presentation of a mitochondrial mutation, and below the levels of heteroplasmy able to cause behavioral defects in mice (26). Importantly, the transfer is compatible with the integrity of the nuclear genome, as it did not result in an increase in copy number variations.

We found that manipulation of an intact spindle-chromosome complex frequently induced premature activation of the oocyte resulting in karyotype abnormalities. Preventing such abnormalities is critical for successful clinical application of nuclear genome transfer, as it is unclear whether visual inspection or even molecular assays can reliably eliminate abnormal embryos. However, exposure of the karyoplast, but not of the cytoplast, to low temperatures prevented manipulation-induced activation. Spindle-chromosome complexes at or below room temperature showed decreased birefringence of microtubules, a measure for the regularity of microtubule alignment. Importantly, upon fusion and incubation at 37° C., spindle birefringence returned, allowing polar body extrusion, normal preimplantation development, and derivation of karyotypically normal stem cells. Such reversible destabilization of spindle microtubules by low temperatures has been previously observed in human and animal oocytes (30, 31). During vitrification of human oocytes, partial depolymerization of the spindle occurs due to the exposure to room temperature, rather than due to the vitrification itself (32). Importantly, cryopreservation, and thereby the exposure of human oocytes to room temperature, does not result in the dispersion of chromosomes and does not increase the incidence of karyotypic abnormalities (33, 34), allowing the adoption for clinical use (35). Tachibana and colleagues (37), using Sendai virus for fusion, found frequent signs of manipulation-induced activation upon transfer of genomes between human oocytes. As a result, more than half of the oocytes were lost due to a failure in polar body extrusion and the formation of karyotypically abnormal embryos (36). In our study, upon fusion with Sendai virus, all oocytes remained at meiosis and extruded the polar body only upon artificial activation. The discrepancy may be explained by small, but significant differences in oocyte handling. Tachibana and colleagues maintain oocytes at 37° C., so as not to destabilize the microtubule spindle, while we briefly expose all oocytes to room temperature (21° C.) prior to enucleation and transfer. An additional difference is the timing of oocyte retrieval at 35 instead of 36 hours post-hCG. Both of these differences likely result in more oocytes with immature spindles at the time of manipulation. Bipolar attachment of chromosomes to spindle microtubules reduces the activity of aurora B kinase and of the spindle assembly checkpoint in a tension dependent manner (38). It is possible that in a fully assembled spindle, manipulation results in a transient increase in tension and decreased kinase target phosphorylation, but not in spindles with incomplete bipolar attachment of chromosomes.

Though concerns have been raised that the transfer of the maternal genome between oocytes may introduce 'epigenetic' changes (39), we did not observe significant differences in gene expression between genome-exchanged and unmanipulated cells. Whilst our methods allow maternal nuclear genome transfer without apparent adverse consequences to the embryo, the accuracy of chromosome segregation at the second meiosis will need to be determined in a large number of samples. Additionally, animal models may be required to determine whether the transfer of incompletely assembled spindles into oocytes is compatible with normal fertilization and development to term. An analogous technique for the transfer of the paternal genome by intracytoplasmic sperm injection (ICSI) is performed in approximately half of all IVF cycles in the USA (40), providing an example for clinical translation. Before proceeding with human clinical trials on the transfer of the maternal genome, it will be important to publicly discuss patient needs, ethical considerations, and to establish appropriate guidelines for the use of oocyte nuclear genome transfer in assisted reproduction.

Illumina array data have been deposited at GEO under accession number GSE42077. Affymetrix array data have been deposited at GEO under accession number GSE42271.

Methods

The nuclear genome was removed from mature MII oocytes and was fused to an enucleated oocyte of a different donor. Oocytes were activated, allowed to develop to the blastocyst stage and stem cells were derived.

Research Subjects

Human oocytes were donated by women enrolled in the reproductive egg donation program at Columbia University Medical Center (CUMC). Oocyte donors were given the option to donate for research only after they had enrolled and qualified as reproductive egg donors. Their decision to donate was therefore independent of the decision to donate for research. Compensation was equivalent to that given for reproductive donation, and did not depend on the number or the quality of oocytes donated, in agreement with ASRM guidelines1. The menstrual cycles of the subjects were synchronized using oral contraceptive pills (OCP). On the third day following the discontinuance of the OCPs, ovarian hyperstimulation was initiated regardless of menstrual flow, using parenterally administered gonadotropins. Once lead follicles reached 18-22 mm diameter, 4 mg leuprolide acetate was administered to trigger final maturation and oocytes were retrieved 35 h later. With each donation, a skin biopsy and 3-4 ml of blood were taken. All human subjects protocols were reviewed and approved by the CUMC IRB and the embryonic stem cell research oversight (ESCRO) committee of CUMC. All oocyte donors gave informed consent.

Manipulation of Human Oocytes

Oocytes were transported in vials containing GMOPSplus (Vitrolife), using a portable incubator heated to 37° C. A total number of 73 MII oocytes were used for this study. Oocytes of different donors were placed in separate drops of GMOPSplus containing 5 μg/ml cytochalasin B (Sigma) covered with mineral oil (Irvine Scientific). Karyoplasts were aspirated into a pipette with a diameter of 20 μm (Humagen), after incubation in medium containing cytochalasin B for 3-5 min. If the karyoplast contained a larger amount of cytoplasm, the additional cytoplasm was removed by pressing the cytoplasm against the zona pellucida. Karyoplasts of donor 1 were inserted below the zona pellucida of an enucleated oocyte of donor 2, and fused using either inactivated Sendai virus HVJ-E (GenomeOne, Cosmo Bio), diluted with fusion buffer 1:40, or electrofusion, performed in cell fusion medium (0.26 M mannitol, 0.1 mM MgSO4, 0.05% BSA, 0.5 mM HEPES) using 2 to 8 fusion pulses of 20 μs width and 1.3 V cm-1 strength (LF201, NEPA Gene). Each exchange required approximately 10 min. Upon aspiration of no more than 2 karyoplasts, transfer was undertaken, unless karyoplasts were used for cryopreservation. All manipulations were performed on a 37° C. heated stage (Tokai Hit) of a Nikon TE 2000U inverted microscope, using Narishige micromanipulators. The transfer of the oocytes from the incubator to the inverted microscope required their brief exposure to room temperature (21° C.). Oocyte culture was conducted in Global medium supplemented with 10% plasmanate (Talecris), or in Global total (LifeGlobal) in a Minc incubator (Cook Medical) infused with a defined gas mixture of 6% CO2, 5% O2, and 89% N2. Parthenogenetic activation of oocytes was done using ionomycin, followed by incubation in 10 μM puromycin for 4 hours. Manipulation of fresh oocytes was usually begun approx. 35 h post hCG, and completed before 40 h post hCG.

Vitrification and thawing of all oocytes was achieved through the use of the cryotop kit (Kitazato) and used in accordance with the manufacturer's instructions on an unheated stage of a Nikon SMZ1500. For vitrification, oocytes were placed into basic solution with equilibrium solution added over a 15 min period. Oocytes were transferred to vitrification solution and then immediately placed onto the cryotop, with minimal solution carry over, and plunged directly into liquid nitrogen.

The cryotop was placed into a protective straw for storage. Upon thawing, the cryotop was quickly placed into pre-warmed (37° C.) thawing solution for 1 min. Oocytes were then transferred into diluent solution (21° C.) and washing solution (21° C.) over a 9 min period after which they were transferred to regular culture medium or GMOP-Splus. 10/11 cryopreserved oocytes were viable upon thawing. Statistical analysis of development and spontaneous activation was undertaken using the Chi-square test. A p-value of <0.05 was considered to be statistically significant.

Stem Cell Derivation and Analysis

Parthenotes were allowed to develop to the expanded blastocyst stage, or day 6 or 7 post activation. The trophectoderm of blastocysts were ablated using the Lykos Laser (Hamilton Thorne), as previously described (2). Isolated ICMs were plated on mouse embryonic fibroblast feeder (MEF) layers in stem cell culture medium (hESm; KO-DMEM with high glucose, supplemented with 20% KSR and bFGF; all cell culture reagents from Life Technologies). For pluripotency analysis, stem cells were fixed and stained for OCT4, SOX2 (both Stemgent), NANOG (Cell Signaling Technology), SSEA3, SSEA4 (both R&D Systems), TRA-1-60 and TRA-1-80 (Millipore). Images were taken using an Olympus IX71 epifluorescence microscope. Live cultures were sent to Cell Line Genetics or WiCell for karyotyping and STR genotyping. Gene expression analysis was undertaken using the Illumina HumanHT-12 Expression Bead-Chip and analyzed using the Illumina Beadstudio software. Quantitative gene expression analysis was undertaken using the Nanostring nCounter system and analyzed using nSolver (Nanostring Technologies). Teratomas were generated by subcutaneous injection into NSG mice (Jackson laboratories) and harvested after 10-15 weeks. Animal experimentation was performed under a Columbia IACUC protocol.

Nuclear and Mitochondrial Genotyping

Samples for both nuclear and mitochondrial genotyping were prepared using the High-Pure Template preparation kit as per the manufacturer's instructions (Roche). Using a range of nDNA and mtDNA primers, PCR products were generated using Red-Taq (Sigma) or Blue Taq (Denville Scientific) as per the manufacturer's instructions and purified using the High-Pure PCR Product Purification Kit (Roche). Sanger sequencing was undertaken via either Genewiz (USA) or Macrogen (USA). Sequences were analyzed using aPe (http://biologylabs.utah.edu/jorgensen/wayned/ape/). Complete mitochondrial genotyping was undertaken using the Affimetrix GeneChip® Human Mitochondrial Resequencing Array 2.0 (MitoChip v.2.0), according to the manufacturer's recommended protocols. Sequences were directly compared to the revised Cambridge Reference Sequence for human mtDNA (NC 012920). Genotyping of nDNA was done using Affymetrix GeneChip Human Mapping 250K NspI arrays according to manufacturer's instructions. Analysis was performed using Affymetrix Genotyping Console.

Copy Number Variation Analysis

Copy number analysis was performed using Affymetrix 6.0 SNP arrays as per the manufacturer's instructions CNVs were detected using NEXUS 6 and the SNP-FASST2 Segmentation algorithm. High gains were set to the threshold of 0.7, gains at 0.1, losses at −0.15 and big losses at −1.1. A significance threshold of 5.0E-7 was used, with minimum number of 10 probes required per CNV call and a minimum size of 50 Kbp (2 Copy losses/gains were analyzed to a minimum of 10 Kbp). Following participation analysis to determine whether CNVs were novel or preexisting, each call was manually inspected for visual confirmation of the call. Either a t-test or one-way ANOVA with Bonferroni's multiple comparison test was used for statistical analysis. A p-value of <0.05 was considered to be statistically significant.

Quantification of mtDNA Copy Number

Quantitative real time PCR analysis of mtDNA copy number was achieved using previously designed primers and calculating unknown samples on a standard curve plotting copy number against a mean threshold value. A standard curve was generated using serial dilutions of a purified-PCR product generated using Red Taq (Sigma) and previously published primers designed for the nucleotide positions 8259-8273 and 8475-84893. Quantification of mtDNA copy number was achieved through the use of primers designed for the nucleotide positions 8290-8308 and 8418-8438. Samples were prepared using the High-Pure Template purification kit as per the manufacturer's instructions although samples were eluted in only 30 µl of elution buffer (Roche). Reaction mixtures were prepared (in triplicate) with 3 µl template DNA, 5 µl 2×SYBR Green PCR Master Mix (Promega), 100 nM of each primer and water to a final volume of 10 µl. The reactions were performed in a Stratagene MX3000P with the following cycle: hold at 95° C. for 10 mins followed by 40 cycles of 95° C. for 15 seconds, 53° C. for 30 seconds, and 72° C. for 1 min. The copy number of an unknown sample was calculated from the standard curve and adjusted for the dilution factor.

Estimation of Oocyte and Karyoplast Volume

Oocytes and karyoplasts were imaged on either an Olympus IX71 or Zeiss LSM5 PASCAL microscope following staining with MitotrackerRed (Life Technologies) and either Hoescht (Sigma) or Draq5 (Biostatus). Single images were taken at the midpoint of each sample of interest, with complete Z-Stacks also imaged. Images were analyzed using Zen LE (Zeiss) and based on the measured diameter, the volume was calculated (with the assumption that oocytes and karyoplasts are spherical).

Quantification of Heteroplasmy Levels: ARMS-qPCR and Last-Hot Cycle RFLP

Heteroplasmy was analyzed using both last hot cycle RFLP and ARMS-qPCR. The presence of three SNPs, m.1670A>T (MT-TV), m.4715A>G (ND2), and m.16129A>G (non-coding region), was validated by Sanger sequencing and the polymorphisms were analyzed by RFLP. The regions flanking the variations site were PCR-amplified. The 305 bp fragment containing the m.4715A variant was digested by BspEI into 2 fragments (204 bp and 101 bp), whereas the m.4715G sequence lacked the BspEI recognition site (FIG. 7a). The 387 bp fragment containing the m.16129A variant was digested by BanI into 2 fragments (176 bp and 211 bp), whereas the m.16129G mtDNA had an additional BanI recognition site yielding 3 fragments (176 bp, 130 bp, and 81 bp) (FIG. 12b—also referred to as Supplementary FIG. 7b). The 312 bp fragment containing the m.1670T variant was digested by AluI in 2 fragments (120 bp and 192 bp), whereas the m.1670A had an additional AluI recognition site yielding to 3 fragments (120 bp, 60 bp, and 132 bp) (FIG. 12c—also referred to as Supplementary FIG. 7c). To assess the heteroplasmy, dCTP [α-32P]—3000 Ci/mmol (Perkin Elmer Health Science, CT) was added to the last PCR cycle, the hot-labeled digested products were electrophoresed in a 10% non-denaturing acrylamide gel, and the bands analyzed in a PhosphorImager (Typhoon TRIO Variable Mode Imager, GE Healthcare Life Science) using ImageQuant™ TL v 7.01 software (GE Healthcare). The experiments were performed in duplicates using oocyte donor fibroblasts (1110 and 1111), in swaPS1 and swaPS2 (passages 2, 9 and 40), in cells differentiated in pancreatic β-cells, and in swaPS3 (passages 4, 5, 6, 8, 10, 13, 14 and 20).

Allele refractory mutation system-qPCR primers were designed to specifically amplify the DNA of only one donor with 2 homozygous SNPS used at either end of the sequence based on the sequencing of hypervariable region 1 (HVR1). Furthermore, the primers were designed such that the product generated would contain internal SNPs that could be verified via Sanger sequencing to confirm donor specific product amplification (FIG. 13a—also referred to as Supplementary FIG. 8a). In order to create a set of standards to confirm accuracy of the assay, the HVR of the various donors was amplified using RedTaq (Sigma) and the product purified with the High Pure PCR Product Purification Kit (Roche). The concentration of PCR product was calculated using a NanoDrop spectrophotometer (NanoDrop Technologies) and the copy number calculated based on a standard curve (101 copies to 107 copies) generated with the assumption that DNA has a molecular mass of 650 Da. From this, standards were generated at various percentages of the two donors to confirm accuracy of the ARMS-qPCR assay. Expected values for the standards were matched against measured values using the equation: Mutant heteroplasmy level $(\%)=1/[1+(1/2)\Delta CT] \times 100\%$ (where $\Delta CT = CT_{wild-type} - CT_{mutant}$ (FIG. 13b-d—also referred to as Supplementary FIG. 8b-d). Upon confirmation, reactions were run under conditions d, e or f with samples of unknown heteroplasmy run alongside positive and negative controls and calculated using the above equation. Samples were run in triplicate in a reaction containing 0.6 ng/µl specific donor sample, 500 nM of each primer, 5 µl of 2×SYBR green (Promega) and water to a final volume of 10 µl and analyzed using a Stratagene MX300P (Agilent). The determination of homoplasmy was undertaken using primers designed around the hypervariable region of donors 1110 and 1111, allowing the incorporation of 5 SNPs per primer pair in order to facilitate in primer specificity. Target DNA was amplified using BlueTaq (Denville Scientific) under cycle conditions k before being analyzed on a 2% agarose gel. Subsequently, 1 µl of the PCR product was diluted 1:100 and re-amplified under the same conditions for a further 30 cycles before being analyzed on a 2% agarose gel.

High-Resolution Northern Blot Analysis

Total RNA from cultured primary fibroblasts grown in a 10 cm2 dish was extracted using Trizol reagent (Life Technologies, Carlsbad, Calif.) according to the manufacturer's instructions. Large RNA species were precipitated by the addition of 10 mol/l LiCl, allowing smaller RNAs to be precipitated from the resulting supernatant. Small RNAs (1.5 μg) were denatured (70° C. for 5 min) and separated through a 8%, 8 mol/l urea denaturing polyacrylamide (19:1) gel using 0.5× Tris Borate EDTA (TBE) as running buffer. Separated samples were electroblotted onto Nytran SuPerCharge TurboBlotter membrane (Whatman, Sanford, Me.) using a TE77X semi-dry transfer unit (Hoefer, Holliston, Mass.) and immobilized by ultraviolet cross-linking. Regions of mtDNA encompassing the tRNAVal and tRNALeu(UUR) genes were amplified using specific primers. Purified PCR products were radiolabeled with α-32P deoxycytidine 5'-triphosphate (3,000 Ci/mmol) by random primer method, and unincorporated nucleotides were removed by gel filtration through a Sephadex G-50 DNA grade column (Amersham Pharmacia Biotech, Uppsala, Sweden). Hybridization was performed at 42° C. overnight using a QuikHyb hybridization solution (Agilent Technologies Stratagene Products Division, La Jolla, Calif.) containing 500,000 cpm radiolabeled probes. After hybridization, two 15 minutes washes were performed at room temperature in 2×SSC and 0.1% SDS, followed by one 30 minutes wash in 2×SSC and 0.1% SDS at 60° C. Blots were subjected to PhosphorImager analysis and the radioactive signal for the mt-tRNAVal probe (69 bp) normalized to the tRNALeu(UUR) signal (75 bp).

Directed Differentiation of swaPS Lines

To confirm the heteroplasmy levels in terminally differentiated tissues, swaPS1 and swaPS2 were differentiated along endodermal, ectodermal and mesodermal lineages. β-cell differentiation was performed as described5, with the addition of calcium chelator, EGTA (75 μM) on day 1 and an activin receptor-like kinase inhibitor, SB431542 (2 μM) on day 9 to 12 of differentiation. Staining for SOX17, PDX1 (both R&D Systems) and C-peptide (Millipore) was undertaken at days 3, 10 and 14. DNA samples for heteroplasmy analysis were collected at day 14. The ectodermal differentiation was undertaken following the previously described dual-SMAD protocol6. After 2 weeks and 2 passages as neural progenitors, further differentiation was induced through the addition of BDNF [10 ng/ml, R&D Systems]. After a further 3 weeks, cells were either fixed for immunostaining or DNA collected for heteroplasmy analysis. Antibodies used for staining included TUJ1 (Sigma), MAP2 (Abcam), Nestin, Neurofilament (both Millipore) and SOX2 (Stemgent). Cells of the mesodermal lineage were generated using 2 protocols. Firstly, the generation of contracting cardiomyocytes (from swaPS1, 2 and 4) was achieved using a previously published protocol7, with videos recorded using an Olympus IX71 with the DP2-BSW software. The differentiation of swaPS1 and swaPS2 into fibroblasts (swaPS-Fibs) was achieved by growing undifferentiated stem cells in hFm for 2-4 weeks with a single passage during this time. After 14-28 days of growth, cells were FACS sorted to enrich for TRA-1-60−/SSEA4−/CD56−/CD13+ cells (FIG. 14a—also referred to as Supplementary FIG. 9a). Antibodies used for staining included α-smooth muscle actin, phalloidin (both Sigma) and CD-13 (BD Biosciences). Gene expression analysis of the swaPS-Fibs was undertaken via the Nanostring nCounter system as previously described. Following differentiation, swapS-Fibs were placed into hESm and grown for 3 weeks on a feeder layer. No colonies were visible during this time period and FACS sorting confirmed the absence of stem cell positive markers indicating swaPS-Fibs could not spontaneously revert to a stem cell state (FIG. 14b-c—also referred to as Supplementary FIG. 9b-c).

Generation of Induced Pluripotent Stem (iPS) Cell Lines

Biopsies were taken using a biopsy kit (AccuPunch, Accuderm Inc.) after local anesthesia using lidocaine (1%, Hospira Inc.). 3 mm punch biopsies were cut into 10-15 small pieces from which fibroblasts were allowed to grow for 4 weeks. Fibroblasts were then passaged using TrypLE and plated in human fibroblast medium (hFm; DMEM supplemented with 10% FBS, 1% Penicillin/Streptomycin and 1% Glutamax) at a density of 50,000 cells per well (6 well plate) overnight before being infected with the Cytotune iPS cell Sendai reprogramming kit as per the manufacturer's instructions (all reagents from Life Technologies). Infected cells were grown in hESm containing 3 additional compounds thiazovivin, SB431542 and PD0325901 (all Stemgent) 4 for ten days before being FACS-sorted to enrich for SSEA4+/Tra-1-60+/CD13− cells. Colonies were picked 7-14 days later and pluripotency was confirmed through the staining of pluripotency markers as described above and Nanostring gene expression analysis as previously described (Supplementary FIG. 9d-g).

Metabolic Analysis

Stem cell lines were transferred from growing on MEFs to Matrigel (BD Biosciences) coated plates and cultured in m-TeSR (Stemcell Technologies). Cells were grown to approximately 90% confluence in 10 cm2 dishes before being harvested and stored at −80° C. Biochemical activities of cytochrome c oxidase (COX or complex IV), NADH-cytochrome c reductase (complex I+III), succinate-cytochrome c reductase (complex II+III), NADH-CoQ reductase (complex I), succinate dehydrogenase (complex II), and citrate synthase (CS) were assayed spectrophotometrically as previously described8. Respiratory chain enzyme activity values were normalized to citrate synthase (CS), an index of mitochondrial mass, and data were expressed as mean±standard deviation (s.d.) of at least 2 experiments. Biochemical activities were measured in 3 pES cell lines, 2 swaPS cell lines, 2 HuES cell lines, and 3 iPS cell lines. Metabolic analysis was also performed in swaPS derived fibroblasts (2 cell lines) compared to control fibroblasts (6 cell lines). One-way ANOVA with Bonferroni's multiple comparison test was used to compare groups. A p-value of <0.05 was considered to be statistically significant. Live metabolic analysis of cells was undertaken using the Seahorse Stress-Test kit as per the manufacturer's instructions. In brief 42,500 cells were seeded into the assay plate and allowed to grow overnight. The following day cells growth media was replaced with XF Assay Medium (Seahorse) supplemented with 25 mM glucose, 0.4% BSA (both Sigma) 1% Glutamax and 1% Sodium Pyruvate (both Invitrogen) for 1 hour. After 1 hour, cells were analyzed using the XF24 (Seahorse). Experiments were performed in duplicates with an n of 4 per group. Results were analyzed using the Seahorse XF24 software One-way ANOVA with Bonferroni's multiple comparison test was used to compare groups. A p-value of <0.05 was considered to be statistically significant.

Example 2

Nuclear Genome Transfer Between Old/Aged and Young Mouse Oocytes

Experiments were performed in which nuclear genomes were transferred between mouse oocytes. The mouse oocytes were "aged" in vitro for differing amounts of time following hCG treatment and were then activated parthenogenetically. Oocytes kept in vitro for only 15 hours post hCG treatment were considered to be "young" while oocytes kept in vitro for 30 hours post hCG were considered "old." In some experiments nuclear genomes were transferred from aged oocytes to young enucleated oocytes, while in others nuclear genomes were transferred from young to aged enucleated oocytes. The results of these experiments showed that development to the blastocyst stage was more efficient after transfer of nuclear genomes into "young" oocytes, as can be seen from the graph provided in FIG. 5. This demonstrates the principal that nuclear genome transfer between oocytes can result in an increased developmental potential.

Materials and Methods.

Cytochalasin B (Sigma) was used for removal of the nuclear genome from the oocyte. GMOPSplus (Vitrolife, #10130) was used to transport oocytes and for manipulation of oocytes. Global (IVF online #LGGG-050) was used to culture oocytes. A certified gas mixture of 5% oxygen, 6% carbon dioxide, and 89% nitrogen (Techair T202250) was used for cell culture. A vitrification kit and a cryotop thawing kit (Kitazato) were used. Humagen micropipets were used for extraction of the oocyte nuclear genome. PCR reagents used for genotyping included: primers (IDT DNA technologies) and RedTaq polymerase (Sigma). Various chemicals (from Sigma) were used: Mannitol, MgSO4, BSA, HEPES buffer (for the generation of a fusion buffer). Ionomycin and puromycin were obtained from Sigma. Inactivated Sendai virus HVJ-E was obtained from GenomeOne, Cosmo Bio. A Roche genomic DNA isolation kit was used. A gene chip Human mapping 250K Nsp Array and assay kit (Affymetrix #900767 and #900766) was used for snp genotyping of donor somatic cell DNA. The following instruments were used for all manipulations: a Nikon T2000-U microscope equipped with a Narishige micromanipulator, Oosight system, and a Tokai hit heating plate. A portable incubator (INC-RB1, CryoLogic) was used to transport oocytes. Electrofusion was performed using an LF201 electrofusion instrument (NepaGene). A Hamilton Thorne Laser system was also used. Additional details of the materials and methods used are provided in Example 1.

Example 3

The present invention involves methods of genome exchange in human oocytes. Applications of these methods include those aimed at preventing transmission of mitochondrial disorders from mother to child, and those aimed at restoring developmental competence to oocytes that are developmentally incompetent. The ability of women to conceive decreases with advanced age. After exhausting other available options, women affected by age-related infertility sometimes resort to oocyte donation. Many years of clinical experience with donation to women of advanced age in the USA has demonstrated that embryos generated from oocytes of young women implanted efficiently in women above the age of 40[64]. This finding suggests that a decrease in oocyte quality is a primary determinant to the drop in fertility as women age[65-67]. Decline in oocyte quality may be determined by a deterioration of the cytoplasm.

Because genome transfer of between human oocytes from two different human subjects requires that oocytes are available on the same day, it can present significant logistical challenges. Oocyte donors and recipients have their professional and private schedules. Even with the best planning, eggs may still need to be retrieved on different days, to obtain oocytes of optimal quality. Cryopreservation will likely be useful for any method of transfer and clinical purpose, for preventing transmission of mitochondrial disorders, for the treatment of infertility, or for other applications.

Figure 15:
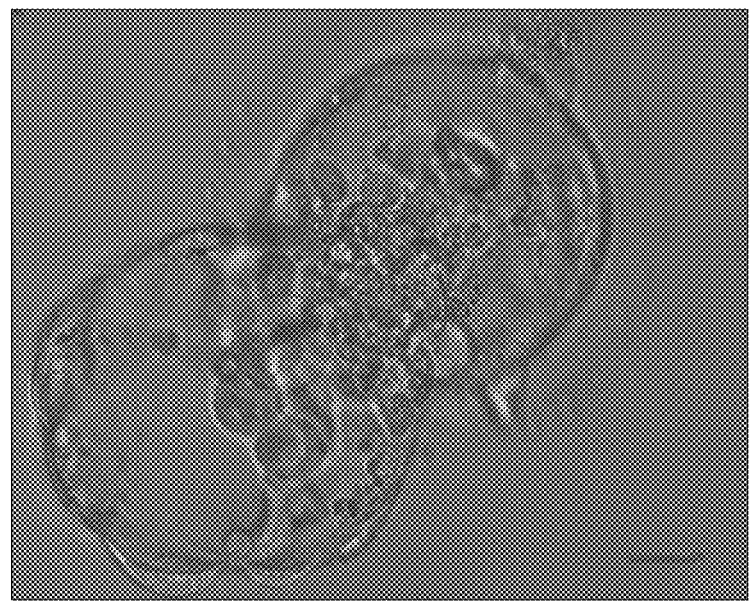
FIG. 15 is a blastocyst derived after genome exchange between oocytes of different donors. Oocytes had been cryopreserved prior to nuclear genome transfer.

In our experiments we used a cryopreservation kit from Kitazato (Japan), but oocytes could be cryopreserved and thawed using any suitable commercially available cryopreservation kit or other suitable cryopreservation method. Mature metaphaseII oocytes from healthy donors were used for these experiments. Upon thaw, oocytes were allowed to recover for approximately 1 hour, then placed on the heated stage of a microscope. 7 of 35 oocytes (20%) developed to the blastocyst stage after parthenogenetic activation. Though this is less efficient than after using newly ovulated oocytes, it shows that cryopreserved oocytes can be used for this purpose. FIG. 15 shows a blastocyst derived after genome exchange between two oocytes (from different individuals) that had been cryopreserved prior to nuclear genome transfer. We are using parthenogenesis for research purposes because it avoids the generation and destruction of potentially viable human embryos. It is an ethical measure that serves as a proof-of-principle. However, we do not anticipate technical differences if standard ICSI or in vitro fertilization methods are used. Three stem cell lines could be derived after genome exchange between thawed oocytes.

REFERENCES

The content of each of these publications is hereby incorporated by reference into the present patent application. The content of each of the publications cited herein is hereby incorporated by reference into the present patent application.

1. Jenuth, J. P., Peterson, A. C., Fu, K. and Shoubridge, E. A. Random genetic drift in the female germline explains the rapid segregation of mammalian mitochondrial DNA. Nat Genet 14, 146-151, doi:10.1038/ng1096-146 [doi] (1996).
2. Bolhuis, P. A. et al. Rapid shift in genotype of human mitochondrial DNA in a family with Leber's hereditary optic neuropathy. Biochemical and biophysical research communications 170, 994-997, doi:papers2://publication/uuid/7C947789-0A8F-4EDA-9B16-4FF0C4CD7828 (1990).
3. Cree, L. M. et al. A reduction of mitochondrial DNA molecules during embryogenesis explains the rapid segregation of genotypes. Nature genetics 40, 249-254, doi:papers2://publication/doi/10.1038/ng.2007.63 (2008).
4. Wai, T., Teoli, D. and Shoubridge, E. A. The mitochondrial DNA genetic bottleneck results from replication of a subpopulation of genomes. Nature genetics 40, 1484-1488, doi:papers2://publication/doi/10.1038/ng.258 (2008).
5. Steffann, J. et al. Analysis of mtDNA variant segregation during early human embryonic development: a tool for successful NARP preimplantation diagnosis. Journal of medical genetics 43, 244-247, doi:papers2://publication/doi/10.1136/jmg.2005.032326 (2006).
6. Bioethics, N. C. o. Novel techniques for the prevention of mitochondrial DNA disorders: an ethical review. (2012). <http://www.nuffieldbioethics.org/mitochondrial-dna-disorders %3E.
7. Sato, A. et al. Gene therapy for progeny of mito-mice carrying pathogenic mtDNA by nuclear transplantation. Proceedings of the National Academy of Sciences of the United States of America 102, 16765-16770, doi:papers2://publication/doi/10.1073/pnas.0506197102 (2005).

8. Tachibana, M. et al. Mitochondrial gene replacement in primate offspring and embryonic stem cells. Nature 461, 367-372, doi:papers2://publication/doi/10.1038/nature08368 (2009).
9. Craven, L. et al. Pronuclear transfer in human embryos to prevent transmission of mitochondrial DNA disease. Nature 465, 82-85, doi:papers2://publication/doi/10.1038/nature08958 (2010).
10. Egli, D. et al. Reprogramming within hours following nuclear transfer into mouse but not human zygotes. Nature communications 2, 488, doi:papers2://publication/doi/10.1038/ncomms1503 (2011).
11. Ganem, N. J., Godinho, S. A. and Pellman, D. A mechanism linking extra centrosomes to chromosomal instability. Nature 460, 278-282, doi:papers2://publication/doi/10.1038/nature08136 (2009).
12. Sathananthan, A. H. et al. Centrioles in the beginning of human development. Proceedings of the National Academy of Sciences of the United States of America 88, 4806-4810, doi:papers2://publication/uuid/CB92B0A2-239F-45EE-8E76-FAA2B73D4FC6 (1991).
13. Kaufman, M. H., Robertson, E. J., Handyside, A. H. and Evans, M. J. Establishment of pluripotential cell lines from haploid mouse embryos. Journal of embryology and experimental morphology 73, 249-261, doi:papers2://publication/uuid/1567470E-A4FC-4679-A7C6-9DA67108D77E (1983).
14. Draper, J. S. et al. Recurrent gain of chromosomes 17q and 12 in cultured human embryonic stem cells. Nature biotechnology 22, 53-54, doi:papers2://publication/doi/10.1038/nbt922 (2004).
15. Kim, K. et al. Histocompatible embryonic stem cells by parthenogenesis. Science 315, 482-486, doi:1133542 [pii] 10.1126/science.1133542 [doi] (2007).
16. Noggle, S. et al. Human oocytes reprogram somatic cells to a pluripotent state. Nature 478, 70-75, doi:papers2://publication/doi/10.1038/nature10397 (2011).
17. Hyun, C. S. et al. Optimal ICSI timing after the first polar body extrusion in in vitro matured human oocytes. Hum Reprod 22, 1991-1995, doi:dem124 [pii] 10.1093/humrep/dem124 [doi] (2007).
18. Brinkley, B. R. and Cartwright, J., Jr. Cold-labile and cold-stable microtubules in the mitotic spindle of mammalian cells. Ann N Y Acad Sci 253, 428-439 (1975).
19. van Oven, M. and Kayser, M. Updated comprehensive phylogenetic tree of global human mitochondrial DNA variation. Hum Mutat 30, E386-394, doi:10.1002/humu.20921 [doi] (2009).
20. Mimaki, M. et al. Reversible infantile respiratory chain deficiency: a clinical and molecular study. Annals of neurology 68, 845-854, doi:papers2://publication/doi/10.1002/ana.22111 (2010).
21. Wang, J., Venegas, V., Li, F. and Wong, L.-J. Analysis of mitochondrial DNA point mutation heteroplasmy by ARMS quantitative PCR. Current protocols in human genetics/editorial board, Jonathan L. Haines . . . [et al.] Chapter 19, Unit 19.16., doi:papers2://publication/doi/10.1002/0471142905.hg1906s68 (2011).
22. Bai, R.-K. and Wong, L.-J. C. Detection and quantification of heteroplasmic mutant mitochondrial DNA by real-time amplification refractory mutation system quantitative PCR analysis: a single-step approach. Clinical chemistry 50, 996-1001, doi:papers2://publication/doi/10.1373/clinchem.2004.031153 (2004).
23. Lee, H. S. et al. Rapid mitochondrial DNA segregation in primate preimplantation embryos precedes somatic and germline bottleneck. Cell Rep 1, 506-515, doi:10.1016/j.celrep.2012.03.011 [doi] (2012).
24. Meirelles, F. V. and Smith, L. C. Mitochondrial genotype segregation during preimplantation development in mouse heteroplasmic embryos. Genetics 148, 877-883 (1998).
25. Jenuth, J. P., Peterson, A. C. and Shoubridge, E. A. Tissue-specific selection for different mtDNA genotypes in heteroplasmic mice. Nat Genet 16, 93-95, doi:10.1038/ng0597-93 [doi] (1997).
26. Sharpley, M. S. et al. Heteroplasmy of Mouse mtDNA Is Genetically Unstable and Results in Altered Behavior and Cognition. Cell 151, 333-343, doi:papers2://publication/doi/10.1016/j.cell.2012.09.004 (2012).
27. Fujikura, J. et al. Induced pluripotent stem cells generated from diabetic patients with mitochondrial DNA A3243G mutation. Diabetologia 55, 1689-1698, doi:papers2://publication/doi/10.1007/s00125-012-2508-2 (2012).
28. Birket, M. J. et al. A reduction in ATP demand and mitochondrial activity with neural differentiation of human embryonic stem cells. Journal of Cell Science 124, 348-358, doi:papers2://publication/doi/10.1242/jcs.072272 (2011).
29. Cowan, C. A. et al. Derivation of embryonic stem-cell lines from human blastocysts. The New England journal of medicine 350, 1353-1356, doi:papers2://publication/doi/10.1056/NEJMsr040330 (2004).
30. Inoue, S., Fuseler, J., Salmon, E. D. and Ellis, G. W. Functional organization of mitotic microtubules. Physical chemistry of the in vivo equilibrium system. Biophys J 15, 725-744, doi:S0006-3495(75)85850-4 [pii] 10.1016/50006-3495(75)85850-4 [doi] (1975).
31. Bianchi, V., Coticchio, G., Fava, L., Flamigni, C. and Borini, A. Meiotic spindle imaging in human oocytes frozen with a slow freezing procedure involving high sucrose concentration. Human reproduction (Oxford, England) 20, 1078-1083, doi:papers2://publication/doi/10.1093/humrep/deh736 (2005).
32. Larman, M. G., Minasi, M. G., Rienzi, L. and Gardner, D. K. Maintenance of the meiotic spindle during vitrification in human and mouse oocytes. Reprod Biomed Online 15, 692-700 (2007).
33. Forman, E. J. et al. Oocyte vitrification does not increase the risk of embryonic aneuploidy or diminish the implantation potential of blastocysts created after intracytoplasmic sperm injection: a novel, paired randomized controlled trial using DNA fingerprinting. Fertility and sterility 98, 644-649, doi:papers2://publication/doi/10.1016/j.fertnstert.2012.04.028 (2012).
34. Gook, D. A., Osborn, S. M., Bourne, H. and Johnston, W. I. Fertilization of human oocytes following cryopreservation; normal karyotypes and absence of stray chromosomes. Hum Reprod 9, 684-691 (1994).
35. ASRM. Mature oocyte cryopreservation: a guideline. Fertil Steril, doi:S0015-0282(12)02247-9 [pii] 10.1016/j.fertnstert.2012.09.028 [doi] (2012).
36. Tachibana, M. and Mitalipov, S. Towards germline gene therapy of inherited mitochondrial diseases. Nature, doi: 10.1038/nature11647 (2012).
37. Tachibana, M., Sparman, M. and Mitalipov, S. Chromosome transfer in mature oocytes. Nat Protoc 5, 1138-1147, doi:nprot.2010.75 [pii] 10.1038/nprot.2010.75 [doi] (2010).
38. Liu, D., Vader, G., Vromans, M. J., Lampson, M. A. and Lens, S. M. Sensing chromosome bi-orientation by spatial separation of aurora B kinase from kinetochore substrates. Science 323, 1350-1353, doi:1167000 [pii] 10.1126/science.1167000 [doi] (2009).

39. Corner, C. A mother's gift, minus mitochondria. Nat Med 16, 645, doi:nm0610-645 [pii] 10.1038/nm0610-645 [doi] (2010).

40. Assisted reproductive technology in the United States: 2000 results generated from the American Society for Reproductive Medicine/Society for Assisted Reproductive Technology Registry. Fertil Steril 81, 1207-1220 (2004).

41. Medicine, E. C. O. T. A. S. F. R. Financial compensation of oocyte donors. Fertil Steril 88, 305-309, doi:S0015-0282(07)00235-X [pii] 10.1016/j.fertnstert.2007.01.104 [doi] (2007).

42. Chen, A. E. et al. Optimal timing of inner cell mass isolation increases the efficiency of human embryonic stem cell derivation and allows generation of sibling cell lines. Cell stem cell 4, 103-106, doi:papers2://publication/doi/10.1016/j.stem.2008.12.001 (2009).

43. Lin, D. P.-C. et al. Comparison of mitochondrial DNA contents in human embryos with good or poor morphology at the 8-cell stage. Fertility and sterility 81, 73-79, doi:papers2://publication/uuid/9E0BD6A4-E12A-4CFD-9838-2BA8DF062AF2 (2004).

44. Lin, T. et al. A chemical platform for improved induction of human iPSCs. Nature Methods 6, 805-808, doi:papers2://publication/doi/10.1038/nmeth.1393 (2009).

45. D'Amour, K. A. et al. Production of pancreatic hormone-expressing endocrine cells from human embryonic stem cells. Nature biotechnology 24, 1392-1401, doi:papers2://publication/doi/10.1038/nbt1259 (2006).

46. Chambers, S. M. et al. Highly efficient neural conversion of human ES and iPS cells by dual inhibition of SMAD signaling. Nature biotechnology 27, 275-280, doi:papers2://publication/doi/10.1038/nbt.1529 (2009).

47. Burridge, P. W. et al. A universal system for highly efficient cardiac differentiation of human induced pluripotent stem cells that eliminates interline variability. PloS one 6, e18293, doi:papers2://publication/doi/10.1371/journal.pone.0018293 (2011).

48. DiMauro, S. et al. Cytochrome c oxidase deficiency in Leigh syndrome. Annals of neurology 22, 498-506, doi: 10.1002/ana.410220409 (1987).

49. Barlow, P., Englert, Y., Puissant, F., Lejeune, B., Delvigne, A., Van Rysselberge, M., and Leroy, F. 1990. Fertilization failure in IVF: why and what next? Hum Reprod 5(4): 451-456.

50. Chen, C. and Kattera, S. 2003. Rescue ICSI of oocytes that failed to extrude the second polar body 6 h post-insemination in conventional IVF. Hum Reprod 18(10): 2118-2121.

51. Egli, D., Birkhoff, G., and Eggan, K. 2008. Mediators of reprogramming: transcription factors and transitions through mitosis. Nat Rev Mol Cell Biol 9(7): 505-516.

52. Egli, D. and Eggan, K. 2010. Recipient cell nuclear factors are required for reprogramming by nuclear transfer. Development 137(12): 1953-1963.

53. Egli, D., Rosains, J., Birkhoff, G., and Eggan, K. 2007. Developmental reprogramming after chromosome transfer into mitotic mouse zygotes. Nature 447(7145): 679-685.

54. Kong, A., Frigge, M. L., Masson, G., Besenbacher, S., Sulem, P., Magnusson, G., Gudjonsson, S. A., Sigurdsson, A., Jonasdottir, A., Wong, W. S. et al. 2012. Rate of de novo mutations and the importance of father's age to disease risk. Nature 488(7412): 471-475.

55. Mitalipov, S. 2010. Methods for Mitochondrial DNA replacement in oocytes. In, USA.

56. Morton, P. C., Yoder, C. S., Tucker, M. J., Wright, G., Brockman, W. D., and Kort, H. I. 1997. Reinsemination by intracytoplasmic sperm injection of 1-day-old oocytes after complete conventional fertilization failure. Fertil Steril 68(3): 488-491.

57. Nagy, Z. P., Joris, H., Liu, J., Staessen, C., Devroey, P., and Van Steirteghem, A. C. 1993. Intracytoplasmic single sperm injection of 1-day-old unfertilized human oocytes. Hum Reprod 8(12): 2180-2184.

58. Ono, T., Mizutani, E., Li, C., Yamagata, K., and Wakayama, T. 2011. Offspring from intracytoplasmic sperm injection of aged mouse oocytes treated with caffeine or MG132. Genesis 49(6): 460-471.

59. Wakayama, S., Thuan, N. V., Kishigami, S., Ohta, H., Mizutani, E., Hikichi, T., Miyake, M., and Wakayama, T. 2004. Production of offspring from one-day-old oocytes stored at room temperature. J Reprod Dev 50(6): 627-637.

60. Woods, J., Bergfelt, D. R., and Ginther, O. J. 1990. Effects of time of insemination relative to ovulation on pregnancy rate and embryonic-loss rate in mares. Equine Vet J 22(6): 410-415.

61. Yuzpe, A. A., Liu, Z., and Fluker, M. R. 2000. Rescue intracytoplasmic sperm injection (ICSI)-salvaging in vitro fertilization (IVF) cycles after total or near-total fertilization failure. Fertil Steril 73(6): 1115-1119.

62. Chen, Z. Q., Ming, T. X., and Nielsen, H. I. 2010. Maturation arrest of human oocytes at germinal vesicle stage. J Hum Reprod Sci 3(3): 153-157.

63. Piette, C., de Mouzon, J., Bachelot, A., and Spira, A. 1990. In-vitro fertilization: influence of women's age on pregnancy rates. Hum Reprod 5(1): 56-59.

64. Navot, D. et al., Poor oocyte quality rather than implantation failure as a cause of age-related decline in female fertility. *Lancet* 337 (8754), 1375-1377. (1991).

65. Klein, J. and Sauer, M. V., Assessing fertility in women of advanced reproductive age. *Am J Obstet Gynecol* 185 (3), 758-770. (2001).

66. Armstrong, D. T., Effects of maternal age on oocyte developmental competence. *Theriogenology* 55 (6), 1303-1322. (2001).

67. van Kooij, R. J., Looman, C. W., Habbema, J. D., Dorland, M., and te Velde, E. R., Age-dependent decrease in embryo implantation rate after in vitro fertilization. *Fertil Steril* 66 (5), 769-775 (1996).

68. Paull, D. et al., Nuclear genome transfer in human oocytes eliminates mitochondrial DNA variants. *Nature* 493 (7434), 632-637 (2013).

The present invention may also be further described and defined in terms of the following claims.

What is claimed is:

1. A method of reducing transmission of a mitochondrial DNA mutation from a mother having the mitochondrial DNA mutation to the mother's offspring, the method comprising using a modified oocyte in an assisted reproduction procedure, wherein the modified oocyte is produced by a method comprising: introducing a nuclear genome from a first oocyte having the mitochondrial DNA mutation into an enucleated second oocyte not having the mitochondrial DNA mutation to form the modified oocyte, wherein the nuclear genome is from a metaphase I oocyte or an immature metaphase II oocyte, and wherein the first oocyte and the second enucleated oocyte are mammalian and from mammals of the same species, thereby preventing or reducing transmission of the mitochondrial DNA mutation.

2. The method of claim 1, wherein the nuclear genome from the first oocyte is an immature metaphase II nuclear genome.

3. The method of claim 1, wherein the nuclear genome from the first oocyte is within a karyoplast.

4. The method of claim 1, wherein the first oocyte and the second oocyte are human oocytes.

5. The method of claim 1, wherein the first oocyte, the second oocyte, or both the first and second oocytes, have been previously cryopreserved.

6. The method of claim 1, wherein the first oocyte is obtained from a subject that has a disease associated with the mitochondrial DNA mutation and the second oocyte is obtained from a subject that does not have the disease.

7. The method of claim 1, wherein the first oocyte is a developmentally incompetent oocyte and the second oocyte is a developmentally competent oocyte.

8. The method of claim 1, wherein the first oocyte is obtained from the mother having the mitochondrial DNA mutation.

9. The method of claim 1, wherein the step of introducing the nuclear genome from the first oocyte into the enucleated second oocyte comprises using an electrical pulse, using a fusogenic agent, or performing microinjection.

10. The method of claim 9, wherein the fusogenic agent is a Sendai virus or polyethylene glycol.

11. The method of claim 1, wherein the nuclear genome has been previously cryopreserved.

12. The method of claim 1, wherein the assisted reproduction procedure comprises an in vitro fertilization (IVF) procedure.

13. The method of claim 1, wherein the assisted reproduction procedure comprises generating an embryo from the modified oocyte.

14. The method of claim 1, wherein the mitochondrial DNA mutation is associated with a disease selected from the group consisting of Kearns Sayre syndrome, Leber's hereditary optic neuropathy and myoclonic epilepsy.

15. The method of claim 1, wherein the nuclear genome from the first oocyte is obtained within 2 hours after extrusion of a first polar body.

16. The method of claim 1, wherein the nuclear genome from the first oocyte is obtained before complete assembly of a metaphase II spindle.

17. A method of reducing transmission of a mitochondrial DNA mutation from a mother having the mitochondrial DNA mutation to the mother's offspring, the method comprising using a modified oocyte in an assisted reproduction procedure, wherein the modified oocyte is produced by a method comprising:
  a) treating a karyoplast comprising a nuclear genome from a first oocyte having the mitochondrial DNA mutation to induce partial spindle depolymerization, wherein the nuclear genome is a mature metaphase II nuclear genome; and
  b) introducing the karyoplast comprising the partially depolymerized spindle into an enucleated second oocyte not having the mitochondrial DNA mutation, thereby producing the modified oocyte, wherein the first oocyte and the second enucleated oocyte are mammalian and from animals mammals of the same species, thereby reducing transmission of the mitochondrial DNA mutation.

18. The method of claim 17, wherein the first oocyte and the second oocyte are human oocytes.

19. The method of claim 17, wherein the first oocyte, the second oocyte, or both the first and second oocytes, have been previously cryopreserved.

20. The method of claim 17, wherein the first oocyte is obtained from a subject that has a disease associated with the mitochondrial DNA mutation and the second oocyte is obtained from a subject that does not have the disease.

21. The method of claim 17, wherein the first oocyte is a developmentally incompetent oocyte and the second oocyte is a developmentally competent oocyte.

22. The method of claim 17, wherein the first oocyte is obtained from the mother having the mitochondrial DNA mutation.

23. The method of claim 17, wherein the step of introducing the nuclear genome from the first oocyte into the enucleated second oocyte comprises using an electrical pulse, using a fusogenic agent, or performing microinjection.

24. The method of claim 23, wherein the fusogenic agent is a Sendai virus or polyethylene glycol.

25. The method of claim 17, wherein the nuclear genome has been previously cryopreserved.

26. The method of claim 17, wherein the assisted reproduction procedure comprises an in vitro fertilization (IVF) procedure.

27. The method of claim 17, wherein the assisted reproduction procedure comprises generating an embryo from the modified oocyte.

28. The method of claim 17, wherein the treatment to induce partial spindle depolymerization comprises cryopreservation, maintaining the nuclear genome at room temperature for up to 4 hours, or contacting the nuclear genome with a microtubule depolymerizing agent.

29. The method of claim 17, wherein the mitochondrial DNA mutation is associated with a disease selected from the group consisting of Kearns Sayre syndrome, Leber's hereditary optic neuropathy and myoclonic epilepsy.

* * * * *